(12) United States Patent
Brand (10) Patent No.: US 12,208,127 B2
(45) Date of Patent: Jan. 28, 2025

(54) PREPARATION AND USE OF CANNABIS NANO-FORMULATION

(71) Applicant: Apurano Pharmaceuticals GmbH, Warngau (DE)

(72) Inventor: Werner Brand, Warngau (DE)

(73) Assignee: Apurano Pharmaceuticals GmbH, Warngau (DE)

( * ) Notice: Subject to any disclaimer, the term of this patent is extended or adjusted under 35 U.S.C. 154(b) by 784 days.

(21) Appl. No.: 17/309,874

(22) PCT Filed: Jan. 5, 2021

(86) PCT No.: PCT/EP2021/050089
§ 371 (c)(1),
(2) Date: Jun. 25, 2021

(87) PCT Pub. No.: WO2021/140101
PCT Pub. Date: Jul. 15, 2021

(65) Prior Publication Data
US 2023/0132438 A1 May 4, 2023

(30) Foreign Application Priority Data
Jan. 6, 2020 (EP) .................................... 20150397

(51) Int. Cl.
*A61K 36/185* (2006.01)
*A61K 9/10* (2006.01)
*A61K 47/24* (2006.01)
*A61K 47/26* (2006.01)
*A61K 47/34* (2017.01)
*A61P 25/04* (2006.01)

(52) U.S. Cl.
CPC ............. *A61K 36/185* (2013.01); *A61K 9/10* (2013.01); *A61K 47/24* (2013.01); *A61K 47/26* (2013.01); *A61K 47/34* (2013.01); *A61P 25/04* (2018.01)

(58) Field of Classification Search
CPC ........ A61K 36/185; A61K 9/10; A61K 47/24; A61K 47/26; A61K 47/34; A61K 31/352; A61K 9/51; A61P 25/04
See application file for complete search history.

(56) References Cited

U.S. PATENT DOCUMENTS

2016/0136213 A1* 5/2016 Paul ...................... A24B 15/26
424/725
2016/0346201 A1* 12/2016 Brand ..................... A61K 33/00

FOREIGN PATENT DOCUMENTS

| JP | 2017-505814 | 2/2017 |
| WO | 2015/114164 | 8/2015 |
| WO | 2016/144376 | 9/2016 |
| WO | 2017/021491 | 2/2017 |
| WO | 2019/104442 | 6/2019 |
| WO | 2019/135224 | 7/2019 |

OTHER PUBLICATIONS

International Search Report issued Mar. 19, 2021 in PCT/EP2021/050089.
Written Opinion issued Mar. 19, 2021 in PCT/EP2021/050089.
Aziz et al., "Supplementation of *Cannabis sativa* L. leaf powder accelerates functional recovery and ameliorates haemoglobin level following an induced injury to sciatic nerve in mouse model", Pakistan Journal of Pharmaceuticals Science, vol. 32, No. 2, Mar. 2019, pp. 785-792.
Japanese Office Action dated Jul. 25, 2023, in Japanese Patent Application No. 2022-541669, with English translation, 8 pages.
European Office Action issued Oct. 5, 2021 in European Application No. 21700361.5.
Patel, et al., "Nanosuspension: An approach to enhance solubility of drugs", Journal of Advanced Pharmaceutical Technology and Research, XP0055090471 2011, pp. 81-87.
Mücke et al., "Cannabis-based medicines for chronic neuropathic pain in adults", Cochrane Database of Systematic Reviews, Issue 3, Art. No. CD012182, 2018, pp. 1-91.
Russian Office Action received for Russian Patent Application No. 2022121324, mailed on Feb. 13, 2023, 23 pages including translation.
Štukelj et al., "Synthesis of stable cannabidiol (CBD) nanoparticles in suspension", Materials and Technology, vol. 53, No. 4, 2019, pp. 543-549.

\* cited by examiner

*Primary Examiner* — Robert A Wax
*Assistant Examiner* — Quanglong N Truong
(74) *Attorney, Agent, or Firm* — Grüneberg and Myers PLLC (57) ABSTRACT

A formulation contains at least one natural *Cannabis* material, at least one solvent, and at least one stabilizer. The formulation is a liquid suspension having a particle size ($D_{90}$) of below 500 nm. The formulation can be used in the treatment of a disease.

22 Claims, 2 Drawing Sheets

PREPARATION AND USE OF CANNABIS NANO-FORMULATION

CROSS-REFERENCE TO RELATED APPLICATIONS

This application is the National Stage entry under § 371 of International Application No. PCT/EP2021/050089, filed on Jan. 5, 2021, and which claims the benefit of European Application No. 20150397.6, filed on Jan. 6, 2020. The content of each of these applications is hereby incorporated by reference in its entirety.

BACKGROUND OF THE INVENTION

Field of the Invention

The present application relates to a formulation comprising at least one natural *Cannabis* material, at least one solvent, and at least one stabilizer, wherein the formulation is a liquid suspension having a particle size ($D_{90}$) of below 500 nm, and the use thereof in the treatment of a disease.

Description of Related Art-Background

The use of *Cannabis* as a natural material in the field of medicine and pharmacy reaches far back in history, as far as 2500 years. However, the use of *Cannabis* products is also associated with fears for possible side effects or addiction. Nevertheless, *Cannabis* was identified as a natural product that may be used as a medicament with advantageous effects. An overview is given in Bridgeman et al., Pharmacy & Therapeutics, vol. 42, 3 (2017), pages 180-188.

SUMMARY OF THE INVENTION

In view of the controversial discussion of the use of *Cannabis* products, and the products currently available not being able to address the needs, there is still a need for a product comprising natural *Cannabis* material which may be safely applied, which has a constant delivery of the active agents to the patient in need thereof, and which shows a pharmacological effect at a lower dose compared to the products available.

The present disclosure addresses these needs. In a first aspect, provided is a formulation comprising at least one natural *Cannabis* material, at least one solvent, and at least one stabilizer, wherein the formulation is a liquid suspension having a particle size ($D_{90}$) of below 500 nm.

A second aspect relates to a formulation for use in palliative care, and/or in the treatment or alleviation of a disease.

The details and further preferred embodiments are disclosed below.

DETAILED DESCRIPTION OF THE INVENTION

In a first aspect, the present disclosure relates to a formulation comprising at least one natural *Cannabis* material, at least one solvent, and at least one stabilizer, wherein the formulation is a liquid suspension having a particle size ($D_{90}$) of below 500 nm.

The formulation of the present disclosure relates to a stable suspension of a natural *Cannabis* material in a solvent. Based on the small particle size of the natural *Cannabis* material, the formulation is particularly suitable for the application to a mammal, in particular a human.

In a second aspect, the present disclosure relates to a formulation for use in palliative care, and/or in the treatment or alleviation of a disease, preferably wherein the disease is selected from the group consisting of pain, in particular acute or chronic pain, somatic pain, visceral pain, neuropathic pain, cancer pain, chronic back pain, chronic central nervous pain; neurological disorders, neurodegenerative diseases, insomnia, psychiatric disorders, nausea, anorexia, vomiting and nausea caused by chemotherapy, diabetic polyneuropathy, fibromyalgia. Tourette-Syndrome, multiple sclerosis, spasm at multiple sclerosis, anxiety disorders, schizophrenia, social phobia, sleep disorder, skin related diseases like psoriasis and neurodermatitis, glaucoma, restless leg syndrome, epilepsy, Alzheimer disease, movement disease like Dystonias, Huntington's disease, Parkinson's disease, bipolar diseases, as well as other medical indications which are affected by the endocannabinoid system and which are affected by any other receptors affected by cannabinoids (e.g. GPR18, GPR119, GPR55).

As further detailed below, based on the use of a natural *Cannabis* material in the formulations of the present disclosure, the formulations may be used as a medicament, in particular in palliative care, and/or in the treatment or alleviation of a disease.

In the following, preferred embodiments of the first and second aspect of the present disclosure are outlined in detail. It is understood that the embodiments are independent of each other and can be freely combined, if not explicitly stated or evident for the skilled person. As an example, preferred embodiments regarding the natural *Cannabis* material are generally independent of preferred embodiments for the solvent or stabilizer, and these embodiments may thus be freely combined.

Formulation

The present disclosure relates to a formulation comprising at least one natural *Cannabis* material, at least one solvent, and at least one stabilizer, wherein the formulation is a liquid suspension having a particle size ($D_{90}$) of below 500 nm. The formulation is present as a liquid suspension, and it may thus also be referred to as suspension or nano-suspension. The nano-suspension comprises particles having a size in the order of nanometers, and it is therefore termed as a nano-suspension. The particles present in the suspension have a particle size ($D_{90}$) of below 500 nm.

In a preferred embodiment of the present disclosure, the particle size ($D_{90}$) of them suspension is below 450 nm, further preferably below 400 nm, still further preferably below 300 nm, still further preferably below 250 nm, and still further preferably below 220 nm. With a smaller particle size of the natural *Cannabis* material in the formulation of the present disclosure, the natural *Cannabis* material can be absorbed more easily, and it is thus more readily available in the body, in particular in the blood plasma.

In a preferred embodiment, the formulation of the present disclosure does not contain a cyclodextrin, or cyclodextrins.

Natural *Cannabis* Material

In the formulation of the present disclosure, a natural *Cannabis* material is present. The natural *Cannabis* material present in the formulation is a natural material, i.e., it is a material grown in nature. Said material is taken from a plant of the family of Cannabaceae, and it is preferably taken from a plant of a genera selected from the group consisting of *Aphananthe, Cannabis, Celtis, Chaetachme, Gironniera, Humulus, Lozanella, Parasponia, Pteroceltis,* and *Trema*. In a particularly preferred embodiment, the material is taken from a plant of genera *Cannabis*.

In a particularly preferred embodiment, the at least one natural *Cannabis* material is a material of the genera *Cannabis*, and the *Cannabis* is a species selected from the group consisting of *Cannabis sativa, Cannabis indica*, and *Cannabis ruderalis*. In other words, according to said embodiment, the plant providing the natural *Cannabis* material is a plant of the species *Cannabis sativa, Cannabis indica*, or *Cannabis ruderalis*. It is particularly preferred that the at least one natural *Cannabis* material is a material taken from a plant of the species *Cannabis sativa*.

As outlined above, the at least one natural *Cannabis* material is taken from a plant of the family of Cannabaceae. In this context, the natural *Cannabis* material may be the entire plant, i.e., the whole of the plant, or other part thereof. Any part of the plant, in particular an entire physiological part of the *Cannabis* plant, may be used as the natural *Cannabis* material. The part of the plant may, according to a preferred embodiment, be selected from the group consisting of leave, stem, seed, flower, root, and mixtures thereof. It is preferred to use the parts of the plant that has a high content of CBD and/or THC. In a particularly preferred embodiment, the part of the plant is the flower of said natural *Cannabis* material.

In a preferred embodiment, the at least one natural *Cannabis* material is a mixture of at least two natural *Cannabis* materials. In other words, different parts of a plant, in particular physiological parts, such as flower or leave, may be used as the natural *Cannabis* material, or the whole or parts of different plants may also be used as the natural *Cannabis* material. The two different plants or parts thereof then together form the natural *Cannabis* material, expressed herein as two natural *Cannabis* materials. The at least two *Cannabis* materials are independently selected from the genera or species defined above. In a particularly preferred embodiment, the natural *Cannabis* material is a mixture of *Cannabis sativa* with *Cannabis* indica or *Cannabis ruderalis*. A mixture of *Cannabis* indica and *Cannabis ruderalis* is less preferred. The content of CBD and/or THC is particularly high in *Cannabis sativa*, which makes this species particularly preferred as natural *Cannabis* material according to the present disclosure.

The natural *Cannabis* material may have a particularly high content of CBD or THC, also referred to as cannabidiol rich material (CBD rich material), or tetrahydrocannabinol rich material (THC rich material). It is understood that the natural *Cannabis* material also refers to material directly derived from the plants. e.g., by drying and/or decarboxylation.

The natural cannabidiol rich material preferably has a cannabidiol concentration in the range from 5 to 40% (w/w), preferably from 10 to 30% (w/w), based on the total mass of cannabinoids in the natural *Cannabis* material.

The natural tetrahydrocannabinol rich material preferably has a tetrahydrocannabinol concentration in the range from 5 to 40% (w/w), preferably from 10 to 30% (w/w), based on the total mass of cannabinoids in the natural *Cannabis* material. In another preferred embodiment, the natural tetrahydrocannabinol rich material preferably has a tetrahydrocannabinol concentration in the range from 5 to 40% (w/w), preferably from 10 to 30% (w/w), based on the total dry mass of the *Cannabis* flower The amount of cannabinoids in the natural *Cannabis* material may vary. Already when taking *Cannabis sativa*, the amount of cannabinoids in the different parts of the plants varies. The amount of cannabinoids in the flowers of *Cannabis sativa* may be in the range of, e.g., 10 to 30% by weight based on the total dry mass of natural *Cannabis* material. Alternatively, the amount of cannabinoids in the flowers of *Cannabis sativa* may be in the range of, e.g., 10 to 30% by weight based on the total dry mass of the *Cannabis* flower.

The natural *Cannabis* material is not merely an extract, i.e., a liquid or soluble fraction of a natural *Cannabis* material, but it is the *Cannabis* material as present in nature in its natural composition of the whole or part of the *Cannabis* plant, milled or ground to a particle size of below 500 nm. The difference to an extract is that the extract, even though it may become solid when the solvent is removed, it may be re-dissolved in a solvent. The natural *Cannabis* material of the present disclosure is present as solid nanoparticulate material in the formulation of the present disclosure. i.e., the formulation of the present disclosure is a suspension, namely small solid particles are suspended in a liquid medium. The solid particles are designed as complex nano-carriers with a hydrophilic coating. The natural *Cannabis* material is thus present in the nano-particles of the suspension of the present disclosure as a solid particle. This is in contrast to encapsulated liquid (oily) materials, such as cannabinoids, which may be encapsulated in, e.g., lipids and/or phospholipids, thereby forming encapsulated liquid droplets (at room temperature).

A suspension is a heterogeneous mixture in which the solid particles do not dissolve, but get suspended throughout the bulk of the solvent, left floating around freely in the medium. The nanoparticles present in the suspension of the present disclosure are encapsulated in a complex nano-carrier with a hydrophilic coating.

However, it is not excluded that, in a preferred embodiment of the present disclosure, the formulation also contains an extract, in particular an extract of a natural *Cannabis* material. Such extract may be used to additionally increase the amount of cannabinoids in the formulation, especially the amount of THC or CBD. It is understood that such extract is in addition to the presence of natural *Cannabis* material as outlined above.

In a preferred embodiment, the natural *Cannabis* material is present in the formulation of the present disclosure in an amount of from 0.1 to 20% (w/w), based on the total mass of the formulation, preferably from 0.1 to 10% (w/w), preferably from 0.2 to 5% (w/w), preferably from 0.3 to 4% (w/w), preferably from 0.5 to 3% (w/w), further preferably from 0.5 to 1% (w/w), from 1 to 2% (w/w), or from 2 to 4% (w/w), based on the total mass of the formulation.

The Particles of Natural *Cannabis* Material

In the formulation according to the present disclosure, particles of at least one natural *Cannabis* material are present. For the preparation of the nano-suspension of the present disclosure, parts or the whole of at least one natural *Cannabis* material is used.

The present formulation is a stable suspension of the at least one natural *Cannabis* material in a solvent by the use of at least one stabilizer. The formulation is thus a heterogeneous mixture of a liquid solvent and the solid natural *Cannabis* material. The natural *Cannabis* material is in the form of nano-particles having a particle size of below 500 nm, stabilized in the solvent by the at least one stabilizer.

The formulation of the present disclosure may be prepared in accordance with the methods disclosed in WO 2015/114164 A1 or WO 2017/021491 A1.

As also outlined below in the Experimental Section, the natural *Cannabis* material may be provided in form of particles having a particle size ($D_{100}$) of below 320 μm. The natural *Cannabis* material, i.e., the particles, may be provided in dry form, in fresh form (i.e., as present in the nature), or containing a specific water content. The powder or particles of natural *Cannabis* material may be added in any of the indicated forms to a solvent in the method of preparation.

In another preferred embodiment, the natural *Cannabis* material as used in the preparation of the nano-suspension may be dried, preferably lyophilized (freeze-dried) and/or thermally dried.

The particles of the natural *Cannabis* material as used for the preparation of the nano-suspension preferably have a low water content. The term "water content" or "residual moisture" as used in the present disclosure refers to the water content w of the material, such as the natural *Cannabis* material, calculated from the mass of the moist or wet material $m_{wet}$ and the mass of the dry material without water $m_{dry}$ and the mass of the material with a residual moisture $m_{res}$ by use of the following formula:

$$\text{residual moisture content } [\%] w = (m_{res} - m_{dry}) / (m_{wet} - m_{dry}) * 100\%$$

In another preferred embodiment, the natural *Cannabis* material as used in the preparation of the nano-suspension has a water content w of below 15% (w<15%), preferably below 10% (w<10%), more preferably below 5% (w<5%), and most preferably below 3% (w<3%).

Such low water content may be advantageous when preparing the nano-suspension. In addition, it may be helpful when bringing the natural *Cannabis* material to a particle size ($D_{100}$) of less than 320 μm. There are different methods known in the art to reduce the water content of a natural *Cannabis* material, and any of these methods may be used in combination with the present disclosure. As an example, the natural *Cannabis* material may be lyophilized (i.e., freeze-dried) or thermally dried. It may be advantageous to clean, peal and/or core the natural *Cannabis* materials, depending on the type of natural *Cannabis* material prior to the drying step.

Natural *Cannabis* materials can be also dried on air or in an oven at a temperature of, e.g., 30 to 140° C. until the residual moisture content w is as low as 5%, or even 3%. Preferably, the drying step is combined with a step of decarboxylation of the active agents in the natural *Cannabis* material, in particular THC and CBD. This may preferably be achieved in an oven at a temperature from 110 to 150° C., preferably from 120 to 140° C. The natural *Cannabis* material may be maintained at the elevated temperature for a period of time ranging from 30 minutes to 5 hours, preferably from 40 minutes to one hour, still further preferably from 45 to 55 minutes.

In another preferred embodiment, the at least one natural *Cannabis* material as used in the preparation of the nano-suspension is pre-ground prior to and/or after the drying, preferably in a knife mill, and optionally sieved to a particle size ($D_{100}$) of less than 320 μm. Such grinding of the natural *Cannabis* material may be done with the natural *Cannabis* material as it is, i.e., without prior cutting or drying, or the natural *Cannabis* material may be cut into pieces and/or dried as described above. Additionally, the natural *Cannabis* material may be sieved in order to provide a powder of natural *Cannabis* material having a particle size ($D_{100}$) of less than 320 μm.

The "total amount of natural *Cannabis* material" contained in the formulation refers to the amount of dry mass, i.e., the mass of dry natural *Cannabis* material without any solvent or stabilizer. The dry mass of the formulation is thus the sum of the dry mass of the particles of at least one natural *Cannabis* material. This is also referred to as the solid matter of the formulation.

Solvent

The formulation of the present disclosure comprises at least one solvent, apart from at least one natural *Cannabis* material, and at least one stabilizer.

In a preferred embodiment, the solvent is selected from the group consisting of water, ethanol, a lipid, an apolar organic solvent, and a mixture thereof, preferably wherein the solvent is a mixture of water and a lipid, e.g., an emulsion. Since the formulation of the present disclosure is preferably a pharmaceutical formulation, the solvent used is preferably a pharmaceutically acceptable solvent. In this respect, particularly preferred solvents are water, ethanol and a mixture of water and a lipid, preferably such mixture of water and lipid. The term "lipid" as used herein refers to a single lipid or a mixture of lipids.

In a further preferred embodiment, the lipid is selected from the group consisting of a solid lipid, liquid lipid, waxes, and a mixture thereof, and still further preferably the lipid is a mixture of a liquid lipid and a solid lipid, in particular when combined with water as solvent.

Accordingly, the resulting formulation may be an aqueous nano lipid formulation, or a nano lipid formulation on the basis of a mixture of solvents (e.g, water, lipids, ethanol). The term "solvent" as used herein refers to a single solvent or a mixture of solvents.

In another preferred embodiment, the solvent is water, preferably distilled water, or a mixture of water and lipids, or a mixture of water and ethanol, or a mixture of water, lipid and ethanol. The water used as solvent may be any kind of water, such as normal water, purified water, distilled water, bi- or tri-distilled water, or demineralized water. It is preferred to use purified water, or any type of distilled water, which fulfills the criteria of a sterilized solvent.

Similarly, the lipids used may be pure lipids, or a nano lipid formulation on the basis of a mixture of water and lipids, a mixture of lipids mixed with water, or a mixture of lipids mixed with water and ethanol. Hence, the nano lipid formulation may contain liquid lipids, solid lipids or a mixture of solid and liquid lipids in varying proportions.

It is most preferred, that the nano smart-lipid formulation is based on a mixture of water and lipids.

Such lipids may be selected from the subcategories of saturated and unsaturated fatty acids, fatty alcohols, waves, fat-soluble vitamins, monoglycerides, diglycerides, triglycerides, sterols and steryl esters, phospholipids and their derivatives, or any other suitable organic compound that is not soluble or not easily soluble in polar solvents.

From the group of triglycerides, liquid lipids, solid lipids, synthetic or semi-synthetic derivatives of glycerol with saturated or unsaturated fatty acids, or a mixture thereof may preferably be selected. Liquid lipids, also known as oils, are typically liquid at room temperature. Solid lipids, also called fats, are usually solid at room temperature and contain a high proportion of unsaturated fatty acids.

In a preferred embodiment, the lipid is a glyceride, preferably selected from the group consisting of monoglycerides, diglycerides, or triglycerides, preferably wherein the lipid is a triglyceride, and more preferably wherein the glyceride is a mixture of a medium-chain triglyceride and glycerol esters of saturated $C_{12}$-$C_{18}$ fatty acids (Gelucire® 39/01).

In a particular preferred embodiment, liquid lipids include medium-chain triglycerides. Other liquid lipids, such as, e.g., tricaprylin, caprylic/capric/linoleic triglycerides, and acetylated monoglycerides may also be selected.

In another preferred embodiment, liquid lipids include natural oils selected from the group consisting of sesame oil, hemp oil, sunflower oil, soybean oil, safflower oil, rapeseed oil (including canola oil), flaxseed oil, nut oil (e.g. almond oil, cashew oil, walnut oil, peanut oil), cottonseed oil, rice bran oil, corn oil, palm oils (including coconut oil), palm kernel oils, marine oils (such as fish oils), and other edible oils.

Solid glycerides include, e.g., hard fats (adeps solidus), Gelucire® 43/01 (Gatefossé, France), tricaprin, trilaurin, trimyristin, tripalmitin, glyceryl tristearates, and—most preferably Gelucire® 39/01 (Gatefossé, France). However, also other solid lipids may be selected, such as Compritol®, Softisan® 378, and cetylpalmitate.

It is particularly preferred that the lipids are selected from the group of triglycerides. Hence, in a particular preferred embodiment, the mixture of lipids for the preparation of the nano lipid formulation comprises or consists of medium-chain triglyceride oil (Lipoid GmbH, Germany) and Gelucire® 39/01 (Gatefossé, France). It is particularly preferred to add the medium-chain triglycerides at a concentration of from 0.1% to 30% (w/w), preferably of from 0.5% to 10% (w/w), further preferably of from 0.1% to 8% (w/w), and the Gelucire® 39/01 at a concentration of from 3 to 20% (w/w), preferably of from 5 to 15% (w/w), based on the total mass of the (final) formulation. All other mono-, di-, and triglycerides, mixtures of those, as well as other suitable lipids may also be selected for the preparation of the present formulation.

Partial glycerides (e.g., glyceryl monostearate, glyceryl monocaprylate, glyceryl monomyristate) and derivatives of oleic acids may also be selected for the preparation of the formulation according to the present disclosure.

From the category of phospholipids, including phosphatidylcholines, phosphatidylserines and glycerolophosphocholines, it is most preferred to use soy bean lecithins, and preferably Lipoid® P45 (Lipoid GmbH, Germany). The formulation of the present disclosure may comprise derivatives of phospholipids, phospholipids derived from synthetic routes, and naturally-occurring food sources selected from e.g. poultry eggs, soya, rapeseed, sunflower, cattle milk, fish eggs, and any combination thereof.

In a particular preferred embodiment, the formulation of the present disclosure comprises a phospholipid, preferably Lipoid® P45, at a concentration of from 1 to 15% (w/w), preferably from 2 to 9% (w/w), based on the total mass of the (final) formulation. In a particular preferred embodiment, the phospholipid contains from 40 to 100% (w/w) phosphatidylcholines, such as Lipoid® H100, Lipoid® P75, Lipoid® P100, and most preferably Lipoid® P45 of Lipoid GmbH, Germany. Other proportions of phosphatidylcholines are also possible.

Stabilizers

The formulation of the present disclosure comprises at least one stabilizer, apart from at least one natural *Cannabis* material, and at least one solvent.

The stabilizer may be selected from the group consisting of phospholipids; polysorbates; polymers comprising homopolymers, block and graft copolymers (comprising hydroxypropyl cellulose (HPC), hydroxypropyl methylcellulose (HPMC), and polyvinylpyrrolidone (PVP)); nonionic tri-block copolymers comprising poloxamers; copolyvinylpyrrolidone; Labrasol®; gelatin; lecithin (phosphatides); gum acacia; xanthan gum; gum arabica; cholesterol; tragacanth: polyoxyethylene alkyl ethers: polyoxyethylene castor oil derivatives: polyoxyethylene sorbitan fatty acid esters: sorbitan fatty acid esters; polyethylene glycols: polyoxyethylene stearates: colloidal silicon dioxide: sodium dodecylsulfate; mono and diglycerides: magnesium aluminum silicate; triethanolamine; stearic acid: calcium stearate; glycerol monostearate; cetostearyl alcohol; cetomacrogol emulsifying wax: short and medium chain alcohols; Labrafil®; Purol-oleique; propane-1,2,3-triol (glycerin): polyvinyl alcohol; dioctyl sodium sulfosuccinate (DOSS); carmellose sodium; carrageen; carbomer; hypromellose; and a mixture thereof.

In a preferred embodiment, the stabilizer is selected from the group consisting of phospholipids, surfactants, and polymers, preferably wherein the stabilizer is a polymer selected from the group consisting of polysorbates, polysaccharides, and poloxamers.

In another preferred embodiment, the stabilizer is selected from the group consisting of phospholipids, polysorbates, propane 1-2,3-triol electrostatic or steric stabilizers, non-ionic surfactants (including polyol esters, polyoxyethylene esters, poloxamers), anionic surfactants (e.g, carboxylates, alkyl sulphates, alkyl ethoxylates, sulfate and sulfate ions), cationic surfactants (e.g. quaternary ammonium compounds), and zwitterionic surfactants.

Some stabilizers are preferably added to the formulation, such as phospholipids, surfactants and emulsifiers (e.g. polysorbates). In a preferred embodiment, the stabilizer is selected from the group consisting of phospholipids; polysorbates, polymers, such as homopolymers, block and graft copolymers (e.g. hydroxypropyl cellulose (HPC), hydroxypropyl methylcellulose (HPMC) and polyvinylpyrrolidone (PVP)); non-ionic tri-block copolymers, such as poloxamers (e.g. Kolliphor® P 407 or poloxamer 188); copolyvinylpyrrolidone: Labrasol®; gelatin; lecithin (phosphatides); gum acacia, xanthan gum: gum arabica: cholesterol, tragacanth; polyoxyethylene sorbitan fatty acid esters; sorbitan fatty acid esters; polyethylene glycols; polyoxyethylene stearates; mono and diglycerides; magnesium aluminium silicate; short and medium chain alcohols: Labrafil® (Gattefossé, France), Labrafil® (Gattefossé, France), propane-1,2,3-triol and polyvinyl alcohol.

In a preferred embodiment, the formulation comprises a polysorbate as stabilizer in an amount of up to 10% (w/w), based on the total mass of the formulation, preferably in an amount of from 0.5 to 4.5% (w/w), in an amount of from 1 to 4.5% (w/w), or in an amount of from 1.5 to 4% (w/w), more preferably in an amount of from 2 to 3% (w/w), or in an amount of from 3 to 4% (w/w), and most preferably in an amount of from 2.5 to 4% (w/w), and/or wherein the formulation comprises a polysorbate as stabilizer selected as polysorbate 80 (Tween® 80) or polysorbate 20 (Tween® 20), preferably polysorbate 80 (Tween® 80).

In another preferred embodiment, the formulation comprises a surfactant as stabilizer in an amount of up to 10% (w/w), based on the total mass of the formulation, preferably in an amount of from 0.5 to 4.5% (w/w), in an amount of from 1 to 4.5% (w/w), or in an amount of from 1.5 to 4% (w/w), more preferably in an amount of from 2 to 3% (w/w), or in an amount of from 3 to 4% (w/w), and most preferably in an amount of from 2.5 to 4% (w/w), and/or wherein the formulation comprises a surfactant as stabilizer selected as sorbitan monooleate (Span® 80).

In still another preferred embodiment, the formulation comprises a poloxamer as stabilizer in an amount of up to 10% (w/w), based on the total mass of the formulation, preferably in an amount of from 0.2 to 1.5% (w/w), more preferably in an amount of from 0.5 to 1% (w/w), and/or wherein the formulation comprises a poloxamer as stabilizer selected as poloxamer 407 (Kolliphor® P407), or poloxamer 188.

In a further preferred embodiment, the formulation comprises a polysaccharide as stabilizer in an amount of up to 5% (w/w), based on the total mass of the formulation, preferably in an amount of from 0.02 to 0.5% (w/w), in an amount of from 0.04 to 0.1% (w/w), more preferably in an amount of from 0.05 to 0.08% (w/w), and/or wherein the formulation comprises a polysaccharide as stabilizer selected as xanthan gum.

In a further preferred embodiment, the formulation comprises a phospholipid as stabilizer in an amount of from 0.5 to 10% (w/w), based on the total mass of the formulation, preferably in an amount of from 1 to 3% (w/w), and/or wherein the phospholipid contains phosphatidylcholine of from 40 to 100 (w/w), based on the total mass of phospholipid, and/or wherein the formulation comprises a phospholipid as stabilizer selected as Lecithin #P45.

The formulation may contain at least one stabilizer, and preferably a mixture of at least two stabilizers. It is particularly preferred that the mixture of stabilizers for the formulation is a mixture of polysorbate 80 (Tween® 80), Kolliphor® P 407 and Lipoid® P45.

When selecting a non-ionic stabilizer, it is preferably selected from the group consisting of non-ionic surfactants, such as polysorbates including polyoxyethylene sorbitane monolaurates; monopalmitates, monostearates, monooleates, tristearates, trioleates, preferably monooleates. Hence, a particularly preferred example for the preparation of the formulation is polyoxyethylene sorbitan mono-oleate (Tween® 80).

Other particularly preferred non-ionic surfactants may be selected from sorbitan monooleates, sorbitan monolaurates, sorbitan monopalmitates, sorbitan monostearates, sorbitan tristearates, sorbitan trioleates, and most preferably sorbitan monooleates (Span® 80).

The non-ionic surfactant, such as polysorbate 80 (Tween® 80) or sorbitan monooleate (Span® 80), is preferably added each individually in an amount of up to 10% (w/w), and further preferred in the range of from 2 to 8% (w/w), and most preferred in the range of from 2 to 6% (w/w), based on the total mass of the formulation.

When steric stabilizers are used as stabilizers, they are adsorbed or attached onto the surface of the nanoparticle providing a large and dense steric barrier. The aim of the steric stabilizer is to overcome attractive Van der Waals forces and therefore reduce particle aggregation, agglomeration or fusion. Steric stabilizers may be selected from polymers such as homopolymers, block and graft copolymers, such as hydroxypropyl cellulose (HPC), hydroxypropyl methylcellulose (HPMC) and polvinylpyrrolidone (PVP).

A particular preferred steric stabilizer is the non-ionic tri-block copolymer Kolliphor® P407, preferably in an amount of up to 4% (w/w), further preferably in an amount of from 0.5 to 3% (w/w), based on the total amount (mass) of the formulation.

Another particular preferred stabilizer that may be used in the formulation of the present disclosure is glycerin (propane-1,2,3-triol). Glycerine is preferably added in an amount of from 10 to 30% (w/w), preferably of from 10 to 20% (w/w) or from 15 to 25% (w/w), based on the total mass of the formulation.

In addition to glycerin, or as alternative thereto, thickeners and stabilizers, such as xanthan gum, gum arabic, carmellose sodium, carrageen, carbomer, hydroxyethylcellulose, hypromellose, methylcellulose, tragacanth may also be used.

In a particular preferred embodiment, xanthan gum is used as stabilizer. The thickener xanthan gum is preferably added to the formulation at a concentration from 0.05% to 1% (w/w), based on the total mass of the formulation.

As can also be gathered from the Examples below, it is particularly preferred that the formulation of the present disclosure contains a combination of stabilizers, i.e., more than one stabilizer.

Additives

Apart from the three essential components of at least one natural *Cannabis* material, at least one solvent and at least one stabilizer, the formulation of the present disclosure may also contain one or more additives as a preferred embodiment. The additives may further add to the long-term stability of the formulation.

In a preferred embodiment, the additive is selected from the group consisting of preservatives, antioxidants, and osmotic agents.

In order to protect the formulation from microbial contamination, the formulation may additionally contain preservatives, or a mixture of preservatives.

In a preferred embodiment, the additive is a preservative, and wherein the preservative is present in the formulation in an amount of from 0.1 to 1% (w/w), based on the total mass of the formulation, preferably in an amount of from 0.10 to 0.15% (w/w), and/or wherein the formulation comprises a preservative as additive selected as potassium sorbate and/or sodium benzoate.

Particularly preferred preservatives are sorbates, such as potassium sorbate, and benzoates, such as sodium benzoate. Most preferred, the formulation may contain the preservatives potassium sorbate and/or sodium benzoate, each individually, at an amount in the range of from 0.1 to 2%, preferably of from 0.5 to 1% (w/w), based on the total amount of the formulation.

Preferred preservatives include benzalkonium chloride, cetylpyridinium chloride, thiomersal, benzoic acid, and propylene glycol. Less preferred preservatives include biguanides (e.g, chlorhexidine), phenols, benzyl alcohols, methyl parabens, ethyl parabens, and propyl parabens.

The formulation of the present disclosure contains cannabinoids which are sensitive to oxidation. It may thus be preferable to further include an antioxidant, or preferably a mixture of at least two or more antioxidants, in the formulation of the present disclosure.

In a preferred embodiment, the additive is an antioxidant, and wherein the antioxidant is present in the formulation in an amount of from 0.001 to 3% (w/w), based on the total mass of the formulation, preferably in an amount of from 0.001 to 0.1% (w/w), in an amount of from 0.005 to 0.1% (w/w), 0.001 to 0.1% (w/w), in an amount of from 0.1 to 1% (w/w), or in an amount of up to 0.02% (w/w), and/or wherein the formulation comprises an antioxidant as additive selected from the group consisting of EDTA, tocopherols, citric acid, and ascorbyl palmitate. In another preferred embodiment, the additive is an antioxidant, and wherein the antioxidant is present in the formulation in an amount of from 0.01 to 3% (w/w), based on the total mass of the formulation.

Most preferred antioxidants include tocopherols, including various types of tocopherols, which differ by the number and position of methyl groups on the benzene ring (e.g. α-tocopherole (E307), γ-Tocopherole (E308)) and particularly preferred a mixture of those (e.g., obtainable form Gustav Parmentier GmbH, Germany).

Furthermore, particularly preferred antioxidants include ascorbic acid and its derivatives, including ascorbic acid and L-ascorbates (e.g., L-ascorbyl palmitate, L-ascorbyl stearate, sodium ascorbate, calcium ascorbate). From the group of ascorbates, L-ascorbyl palmitate is particularly preferred.

In addition, other preferred antioxidants are ethylenediaminetetraacetic acid, and derivatives of ethylenediaminetetraacetic acid, such as calcium disodium ethylenediaminetetraacetic acid. When ethylenediaminetetraacetic acid is used, it is most preferably added in combination with ascorbyl palmitate, or derivatives thereof.

Ethylenediaminetetraacetic acid is preferably added at an amount in the range of from 0.01 to 1% (w/w), preferably 0.05 to 0.6% (w/w), and ascorbic palmitate in an amount of from 0.01 to 0.3% (w/w), based on the total amount of the formulation.

In a particularly preferred embodiment, the formulation contains a mixture of antioxidants for achieving a synergistic antioxidative effect.

In another preferred embodiment, the formulation contains a mixture of following antioxidants: tocopherols, ascorbic palmitate and ethylenediaminetetraacetic acid.

Alternatively, Coenzyme Q10, gallates (e.g. propyl gallate), and less preferred derivatives of phenol, such as butylated hydroxyanisole, butylated hydroxyl toluene, and t-butylhydroquinone, may also be added to formulation.

The formulation of the present disclosure may also contain additives to regulate its pH. Such pH regulatory agents may be any buffers know, and in a preferred embodiment, citric acid is used. In another preferred embodiment, the formulation may contain a compounds selected from the group consisting of lactic acid and lactates, phosphoric acid and phosphates, hydrochloric acid, and hydroxide salts. If citric acid is used, it may be added to the formulation in an amount of from 0.1 to 3% (w/w), preferably of from 0.2 to 1.5% (w/w), based on the total amount of the formulation.

The formulation of the present disclosure may further comprise an osmotic agent, preferably selected from the group consisting of glycerin, glucose, sucrose, sorbitol, sodium phosphate and any combination thereof.

Diseases

The formulation of the present application may be used for the treatment or alleviation of diseases or conditions in an animal, preferably a mammal, further preferably a human. The diseases that can be treated with the formulation according to the present disclosure are cannabinoid related diseases or conditions, based on the presence of a natural Cannabis material in the formulation.

Cannabis triggers a complex set of experiences in humans including euphoria, heightened sensitivity to external experience, and relaxation. The pharmacological effects of medical Cannabis presently used are mainly due to the two main ingredients of the hemp plant, the phytocannabinoids tetrahydrocannabinol (THC) and the primary non-euphorizing and non-addictive compound cannabidiol (CBD). Until now, Cannabis research has focused mainly on these two ingredients. The content of the THC and CBD and the ratio to each other differs depending on the plant variants. There are, e.g., Cannabis plant species available with about 22% THC, but also species with a content less than 1% THC and 20% CBD. Since THC and CBD have different pharmacological effects, these Cannabis plant species are used for different therapeutic algorithms. Molecules such as THC and CBD may offer novel targets for the development of effective and durable therapies for numerous diseases. Besides THC and CBD, Cannabis flowers contain numerous additional pharmacologically active phytochemicals, such as Cannabichromen (CBC), Cannabigerol (CBG), Tetrahydrocannabivarin (THCV), Cannabidivarin (CBDV) and Cannabinol (CBN). The plant contains various terpenes with therapeutic potential, such as D-limonene, β-myrcene, α-pinene, D-linalool, β-caryophyllene. Terpenes are a highly heterogeneous group of substances. Terpenes may act synergistically with phytocannabinoids. The Cannabis plant contains more than 200 terpenes and terpenoids with different pharmacologic properties. The terpenes add the characteristic smell and taste to Cannabis.

Cannabinoid receptors are activated by phytocannabinoids, synthetic cannabinoids, and endocannabinoids. Cannabinoids bind reversibly and stereo-selectively to the cannabinoid receptors. Cannabinoid receptors are located throughout the body and are part of the endocannabinoid system, which is involved in a great variety of physiological processes. Cannabinoid receptors are G protein-coupled receptors containing seven transmembrane spanning domains. The CBI receptor is expressed mainly in the central nervous system, but also in the lungs, liver and kidneys. The CB2 receptor is expressed mainly in the immune system and in hematopoietic cells. There is evidence that there are also other (G protein-coupled) non-CB1- and non-CB2-cannabinoid receptors (GPR18, GPR119 and GPR55) involved in the signalling of the endocannabinoid system. Endocannabinoids, such as anandamide (AEA) and arachidonoylethanolamide (2-AG), are produced and cleaved from nerve cell membrane lipid precursors following depolarization of the postsynaptic membrane and/or activation of postsynaptic metabotropic receptors. The endocannabinoids diffuse retrogradely to their receptors located at the afferent nerve fibers Endocannabinoid signaling is terminated by cellular uptake processes, which likely involve transporter proteins, followed by intracellular hydrolysis of 2-AG by presynaptic monoacylglycerol lipase (MGL) and of AEA by postsynaptic fatty acid amide hydrolase (FAAH). It remains to be shown that the same processes apply to all of the different neuronal populations expressing CBI receptors. Noteworthy, AEA may additionally bind to cytosolic domains of postsynaptically localized Transient Receptor Potential Vanilloid Type-1 (TRPV1) channels, thereby promoting activation of postsynaptic terminals. CBD and THC are multitarget ligands and behave as allosteric modulators of AEA and 2-AG. Recent studies showed that CBD does not bind directly to CBI and CB2. CBD enhances morphine antinociception, diminishes NMDA-mediated seizures and reduces stroke damage via the sigma 1 receptor. Notably, sigma 1 receptor (σ1R) antagonists inhibit glutamate N-methyl-D-aspartate acid receptor (NMDAR) activity. The sigma-1 receptor (σ1R) acts as a chaperone protein at the endoplasmic reticulum that modulates calcium signalling through the IP3 receptor. The σ1-receptor is a transmembrane protein, expressed in many different tissue types. It is particularly concentrated in certain regions of the central nervous system. Synthetic compounds, amines as well as neuroactive steroids, such as dehydroepiandrosterone (DHEA) and pregnenolone activate the receptor. In an in vitro assay, CBD disrupted the regulatory association of σ1R with the NR1 subunit of NMDAR, an effect shared by σ1R antagonists, such as BD1063 and progesterone, and prevented by σ1R agonists, such as 4-IBP, PPCC and PRE084. CBD displays antagonist-like activity toward σ1R to reduce the negative effects of NMDAR overactivity: CBD alleviates NMDA-induced convulsive syndrome, reduces the infarct size caused by permanent unilateral middle cerebral artery occlusion and enhances morphine-evoked supraspinal antinociception.

The pain pathophysiology includes peripheral and central neuronal alterations as well as neuro-immune interactions, which become more prominent during inflammatory reactions. Nociception (acute pain) produces lasting effects in the sensory and the reward circuitry of the brain. Chronic pain is the abnormal persistent memory of an aversive state (Memory of Pain) and autobiographical memories may be illustrated as the ghosts of our past. Most importantly, chronic pain is not the same as acute nociception that lasts longer. Chronic pain is a disease process with different mechanisms associated with anxiety and depression.

The modification of a dysfunctional cognition by cannabinoids is a novel therapeutic approach in the therapy of chronic pain states. Noxious stimuli engage a central circuit operated by endocannabinoids. Brain areas, which play an important role in higher cognitive processes, and in the regulation of stress-induced activity, contain a high density of the various cannabinoid receptors. Human brain imaging studies indicate that cortical and sub-cortical fear conditioning pathways may be fundamental to chronic pain. Emotion-related limbic circuits play an important role in higher cognitive processes, and in the regulation of stress-induced hypothalamic-pituitary-adrenal (HPA) activity Excessive fear and anxiety are also characteristic of disorders such as post-traumatic stress disorder (PTSD) and phobias. PTSD is characterized by persistence of fear memories and maladaptive stress responses. The potential therapeutic benefits of cannabinoid compounds have also raised interest in understanding the molecular mechanisms that underlie the beneficial effects of exposure therapy in phobic disorders. The addition of CBD to exposure therapy is expected to strengthen effects of treatment.

Human brain imaging studies indicate that the brain is more plastic than previously believed and formation of new synapses and new dendritic processes of nerve cells, so-called spines, occur continuously. Spines are the target structure of most excitatory synapses in the brain and are functionally and structurally highly dynamic during development, but also in adulthood. The brain structures involved in social pain and physical pain are similar. Chronic pain triggers chronic stress responses such as dendritic regression and loss of dendritic spines in brain neurons that is accompanied by deficits in synaptic plasticity and memory. It may predispose patients to disordered cognition.

The molecular composition of the cannabinoid type 1 (CB1) receptor complex beyond the classical G-protein signalling components is not known. The CBI receptor assembles with multiple members of the WAVE1 complex and the RhoGTPase Rac1 and modulates their activity. Activation levels of CBI receptor directly impact on actin polymerization and stability via WAVE1 in growth cones of developing neurons, leading to their collapse, as well as in synaptic spines of mature neurons, leading to their retraction. In adult mice. CBI receptor agonists attenuate activity-dependent remodeling of dendritic spines in spinal cord neurons in vivo and suppressed inflammatory pain by regulating the WAVE1 complex. This study reports novel signalling mechanisms for cannabinoidergic modulation of the nervous system and demonstrates a previously unreported role for the WAVE1 complex in therapeutic applications of cannabinoids. These recent advances in pain research illustrate the analytical power of molecular and cellular biological techniques in a field previously accessible only to methods of systems biology. Abnormal dendritic spine structure following disease or injury may represent a "molecular memory" for maintaining e.g, chronic pain states sensitive to cannabinoid modulation of spine function. At a conceptual level, a memory mechanism that engages dendritic spine remodelling by cannabinoids would contribute to a broad range of intractable neurological conditions.

Long-term memory formation and storage are complex and dynamic processes. Molecular and cellular mechanisms underlie this complexity, e.g, their expression in diverse cell types, their temporal dynamics their roles in long-term memory formation, and storage, as well as changes induced by memory recall. Repeated exposure to a feared stimulus in the absence of an aversive event leads to a gradual reduction in the fear response (Extinction by Re-learning). The activation of CBI specifically located on GABAergic interneurons inhibits LTD in the lateral amygdala. These findings suggest that CBI receptors expressed on either glutamatergic or GABAergic neurons play a differential role in the control of synaptic transmission and plasticity. The results indicate that AEA decreases the activity of inhibitory interneurons in the amygdala. This disinhibition increases the activity of common output neurons and could provide a prerequisite for "extinction" by formation of new memories.

Recent research has increasingly detailed the brain's capacity for reorganization of neural network architecture to adapt to environmental needs. A core set of brain networks is commonly disturbed with chronic pain. All strategies for the treatment of chronic pain conditions must consider stress related comorbid conditions such as the altered hedonic state, disordered cognition and aberrant behaviours such as fear, anxiety and depression. The emotional basis of chronic pain opens up a new horizon of opportunities for developing new treatment strategies since cognitive factors such as beliefs, expectations and prior experience are key modulators of the perception of pain and can substantially modulate the efficacy and tolerability of therapeutic interventions. Accumulating evidence points to brain reorganization (neuronal plasticity) with this negatively valenced affective state. Chronic pain appears as the dark side of neuronal plasticity. The memory of pain can be more damaging than its initial experience.

Human studies and multiple animal pain models support the view that therapeutic interventions with cannabinoids should intercept with chronification processes as early as possible. The anxiolytic and anti-stress effects of cannabinoids will provide the gateway to a successful multimodal therapy since e.g, the experience-based adaptation of expectancies (Memory of Pain) is best countered by overlaying it with positive new associations. They create new links in neuronal circuits and will help re-learning of context-specific safety signals. The regained ability to derive pleasure from ordinary activities is extremely important. The gradual fading of memories is an important part of memory processing. However, fear memories may be actively protected in various brain structures Fear conditioning induces apparently memory traces, more resilient to erasure and conditioned fear responses can recover spontaneously after a re-exposure to the aversive stimulus. The brain has no simple erase function.

Concluding from the above, *Cannabis*, i.e., a natural *Cannabis* material as present in the formulation of the present disclosure, is related to treat the following diseases:

Somatic pain: the feeling most people imagine when they think about pain: a message sent by receptors located throughout the body whenever injury occurs. Somatic pain signals travel to the brain via peripheral nerves, and are typically experienced as a constant, dull ache in the injured region.

Visceral pain: occurring when tissues or organs in the abdominal cavity become stretched or otherwise disturbed due to disease or injury. Pain signals issue from a specific class of receptors present in the gut, producing feelings of pressure deep within the abdomen. Visceral pain often seems to be coming from a different part of the body than its actual source, a phenomenon known as referred pain.

Neuropathic pain: occurring when nerves themselves sustain injury. It is often experienced as a burning sensation that can occur in response to even a gentle touch. Neuropathic pain does not usually respond to narcotic painkillers, which relieve many other types of pain. Antidepressant or anticonvulsant drugs, as well as certain surgical procedures, may improve some cases of neuropathy.

Cancer pain

Vomiting and nausea caused by chemotherapy

Chronic back pain

Diabetic polyneuropathy

Fibromyalgia

Palliative care

Tourette-Syndrome

Chronic central nervous pain

Spasm at multiple sclerosis

Anxiety disorder

Schizophrenia

Social phobia

Sleep disorder

Skin related diseases like psoriasis and neurodermatitis

Glaucoma

Restless leg syndrome

Epilepsy

Alzheimer's disease

Movement disease like Dystonias, Huntington's disease, Parkinson's disease

Accordingly, the formulation of the present disclosure may in particular be useful in the treatment or alleviation of one of the diseases listed above.

In a preferred embodiment, the formulation of the present disclosure may be used in palliative care, and/or in the treatment of a disease, preferably wherein the disease is selected from the group consisting of pain, in particular acute or chronic pain, somatic pain, visceral pain, neuropathic pain, cancer pain, chronic back pain, chronic central nervous pain; neurological disorders, neurodegenerative diseases, insomnia, psychiatric disorders, nausea, anorexia, vomiting and nausea caused by chemotherapy, diabetic polyneuropathy, fibromyalgia, Tourette-Syndrome, multiple sclerosis, spasm at multiple sclerosis, anxiety disorders, schizophrenia, social phobia, sleep disorder, skin related diseases like psoriasis and neurodermatitis, glaucoma, restless leg syndrome, epilepsy, Alzheimer disease, movement disease like Dystonias, Huntington's disease, Parkinson's disease, as well as other medical indications which are affected by the endocannabinoid system and which are affected by any other receptors affected by cannabinoids (e.g. GPR18, GPR119, GPR55).

Based on the small particle size of the natural *Cannabis* material in the formulation, the present disclosure provides a formulation according to the first aspect for use in the preparation of a medicament, in particular for buccal, mucosal, oromucosal, topical or oral application to an animal, preferably a mammal, further preferably a human, or for use in the preparation of a medicament for parenteral, intrathecal, intravenous, transdermal, or trans-mucosal application, preferably buccal, topical or oral application, to an animal, preferably a human.

Definitions

In the following, a number of definitions of terms is given as they are used in the context of the present disclosure.

Where the term "comprising" is used in the present description, it does not exclude other elements. For the purposes of the present invention, the term "consisting of" is considered to be a preferred embodiment of the term "comprising". If hereinafter a group is defined to comprise at least a certain number of elements, this is also to be understood to disclose a group, which preferably consists only of these elements.

Where an indefinite or definite article is used when referring to a singular noun, e.g. "a", "an" or "the", this includes a plural of that noun unless specifically stated otherwise.

The term "at least one" refers to a number of 1 or more representations of the following term, in particular natural *Cannabis* material, solvent and stabilizer. The representations of the respective material, if present more than once, i.e., 2, 3, 4, or more times, may be independently selected from each other within the definition of the respective material. In particular, at least one refers to 1, 2, 3, 4 or 5 independently selected representations of the respective material, particularly preferred 1 or 2 times.

Terms like "obtainable" or "definable" and "obtained" or "defined" are used interchangeably. This, e.g., means that, unless the context clearly dictates otherwise, the term "obtained" does not mean to indicate that e.g, an embodiment must be obtained by e.g, the sequence of steps following the term "obtained" even though such a limited understanding is always included by the terms "obtained" or "defined" as a preferred embodiment.

"THC" refers to tetrahydrocannabinol, and it comprises all types of isomers of tetrahydrocannabinol, but in particular refers to 49-THC.

"CBD" refers to cannabidiol. Cannabidiol is one of the major cannabinoids in *Cannabis*, and it the active agent with most interest in the community.

$D_{90}$ relates to the particle size distribution of the formulation. It refers to the volume of the particles where 90% of the total volume of the particles (volume, $D_{V90}$) have a smaller size than the given number, and 10% of the volume consists of particles having a larger size than the given number. In other words, 90% of the total volume of particles are formed of particles of a diameter smaller than $D_{90}$, the residual 10% of the total volume of particles are formed of particles of a diameter larger than $D_{90}$. As an example, if $D_{90}$ is 500 nm, particles having a size smaller than or equal to 500 nm constitute for 90% of the total volume of the sample, and particles having a particle size larger than 500 nm constitute for 10% of the total volume of the sample.

$D_{100}$ refers to the maximum size of the particles. In other words, 100% of the particles have a size smaller than or equal to the given particle size.

Tween® 80 is the tradename of Polysorbate 80, also termed as Polyoxyethylen(20)-sorbitan-monooleat.

Span® 80 is the synonym of sorbitan monooleat, a sorbitan fatty acid ester of sorbit or 1,4 sorbit anhydride (sorbitan) with a fatty acid, such as stearic acid, lauric acid, oleic acid, or palmitic acid.

Kolliphor® P407 (poloxamer 407) and poloxamer 188 both belong to the group of poloxamers, and they are defined in the Europäisches Arzneibuch, Deutscher Apotheker Verlag Stuttgart, 6$^{th}$ edition, 2008, pages 3713-3715. Poloxamers are block co-polymers of ethylene oxide and propylene oxide.

Lipoid® P45 is a fat-free soybean lecithin with an amount of phosphatidylcholine of 45% (w/w).

Labrafil® is a tradename (Gattefossé) for oleoyl polyoxyl-6 glycerides.

Labrasol® is a tradename (Gattefossé) for caprylocaproyl polyoxyl-8 glycerides.

Gelucire® 39/01 is a mixture of medium-chain mono-, di- and triglyceride, i.e. glycerol esters of saturated C'12- Cis fatty acids.

EXPERIMENTAL SECTION

In the following, the present invention is illustrated in more detail with reference to the following examples. The following examples are set forth to assist in understanding the disclosure and should not be used as specifically limiting the disclosure described herein. Such variations of the disclosure, including the substitution of all equivalents now known or later developed, would be within the purview of those skilled in the art, and changes in formulation or changes in experimental design, are to be considered to fall within the scope of the disclosure incorporated herein.

Example 1: Stable Formulation of Cannabidiol Rich *Cannabis sativa* (1% (w/w))

Pre-ground and steam sterilized flower plant material from a cannabidiol rich *Cannabis sativa* strain (A6FS10 flos, AI Fame, Switzerland, $D_{90}$<320 µm, residual moisture <10%) was used as *Cannabis* powder.

The *Cannabis* powder was inserted into a pre-heated oven chamber at 135° C. When the *Cannabis* powder has reached a core temperature of 120° C., the powder was subsequently heated for further 55 minutes at 135° C., in order to achieve decarboxylation of the active ingredients. This step further reduces the residual moisture in the *Cannabis* powder.

The amount of all ingredients is given in % (w/w), based on the total amount (mass) of the final nano-suspension.

10.5% (w/w) Gelucire® 39/01 was pre-heated in a tempered water bath at 70° C., for one hour and 30 minutes.

Separately, 0.7% (w/w) sodium benzoate, 0.6% (w/w) potassium sorbate, 0.1% (w/w) ethylenediaminetetraacetic acid, and 0.5% (w/w) citric acid were dispersed and thoroughly mixed in 56.69% (w/w) bi-distilled water and also pre-heated at 70° C., for one hour.

1.2% (w/w) medium chain triglyceride oil, 2% (w/w) Kolliphor® P407, 0.05% (w/w) ascorbyl palmitate, 0.06% (w/w) mixed tocopherols (Vitapherole®), 4.8% (w/w) polyoxyethylene sorbitan monooleate 80 (Tween® 80) and 5.8% (w/w) Lipoid #P45 were mixed in a separate container.

All above listed compounds (except *Cannabis* powder) were combined in a suitable vessel at a temperature of 70° C.

Subsequently, 1% (w/w) decarboxylated and sterilized pre-ground *Cannabis sativa* powder material as prepared above ($D_{90}$<320 µm, residual moisture <3%) was carefully added to the degassed mixture and dispersed under continuous stirring. When dispersing the *Cannabis* material in the solvent, the *Cannabis* material in the formulation had a concentration of 1% (w/w), based on the total mass of the formulation.

Again, the vessel containing all ingredients was degassed until an oxygen partial pressure of below 1.5 hPa was achieved. The dispersion was subsequently milled in a wet ball agitator mill (type X1, Buehler AG, Switzerland; 1000-1200 rpm, 45° C.) using yttrium stabilized zirconia balls of size 0.4 to 0.5 mm. The milling was continued until a monomodal particle size distribution of below 0.4 µm ($D_{100}$) was achieved. Subsequently, 16% (w/w) glycerin was added and milling was continued until reaching the final particle size ($D_{90}$) of the formulation of below 0.2 µm (200 nm) as measured by the laser diffraction device Beckman-Coulter LS13320.

TABLE 1

Ingredients and amounts used in the formulation of Example 1.

| Ingredient | Amount [% (w/w)] |
| --- | --- |
| Cannabis powder | 1 |
| Gelucire ® 39/01 | 10.5 |
| Sodium benzoate | 0.7 |
| Potassium sorbate | 0.6 |
| Ethylenediaminetetraacetic acid | 0.1 |
| Citric acid | 0.5 |
| Bi-distilled water | 56.69 |
| Medium chain triglyceride oil | 1.2 |
| Kolliphor ® P407 | 2 |
| Ascorbyl palmitate | 0.05 |
| Mixed tocopherols | 0.06 |
| Polyoxyethylene sorbitan monooleate 80 | 4.8 |
| Lipoid ® P45 | 5.8 |
| Glycerin | 16 |
| Total | 100 |

Example 2: Stable Formulation of Tetrahydrocannabinol Rich *Cannabis sativa* (2% (w/w))

Pre-ground and steam sterilized flower plant material from a tetrahydrocannabinol rich *Cannabis sativa* strain (Bedrocan flos, Bedrocan, Netherlands), $D_{90}$<320 µm, residual moisture <10%) was used as *Cannabis* powder.

The *Cannabis* powder was inserted into a pre-heated oven chamber at 135° C. When the *Cannabis* powder has reached a core temperature of 120° C., the powder was subsequently heated for further 55 minutes at 135° C., in order to achieve decarboxylation of the active ingredients. This step further reduces the residual moisture in the *Cannabis* powder.

The amount of all ingredients is given in % (w/w), based on the total amount (mass) of the final nano-suspension.

13.5% (w/w) Gelucire® 39/01 was pre-heated in a tempered water bath at 70° C., for one hour and 30 minutes.

Separately, 0.7% (w/w) sodium benzoate, 0.6% (w/w) potassium sorbate, 0.15% (w/w) ethylenediaminetetraacetic acid, and 0.6% (w/w) citric acid were dispersed and thoroughly mixed in 48.42% (w/w) bi-distilled water and also pre-heated at 70° C., for one hour.

1.6% (w/w) medium chain triglyceride oil, 2.3% (w/w) Kolliphor® P407, 0.07% (w/w) ascorbyl palmitate, 0.06% (w/w) mixed tocopherols (Vitapherole®), 5.2% (w/w) polyoxyethylene sorbitan monooleate 80 (Tween® 80) and 6.8% (w/w) Lipoid® P45 were mixed in a separate container.

All above listed compounds (except *Cannabis* powder) were combined in a suitable vessel at a temperature of 70° C.

Subsequently, 2% (w/w) decarboxylated and sterilized pre-ground *Cannabis sativa* powder material as prepared above ($D_{90}$<320 μm, residual moisture <3%) was carefully added to the degassed mixture and dispersed under continuous stirring. When dispersing the *Cannabis* material in the solvent, the *Cannabis* material in the formulation had a concentration of 2% (w/w), based on the total amount of the formulation.

Again, the vessel containing all ingredients was degassed until an oxygen partial pressure of below 1.5 hPa was achieved. The dispersion was subsequently milled in a wet ball agitator mill (type X1, Buehler AG. Switzerland: 1000-1200 rpm, 45° C.) using yttrium stabilized zirconia balls of size 0.4 to 0.5 mm. The milling was continued until a monomodal particle size distribution of below 0.4 μm ($D_{100}$) was achieved. Subsequently, 18% (w/w) glycerin was added and milling was continued until reaching the final particle size ($D_{90}$) of the formulation of below 0.2 μm (200 nm) as measured by the laser diffraction device Beckman-Coulter LS13320.

TABLE 2

Ingredients and amounts used in the formulation of Example 2.

| Ingredient | Amount [% (w/w)] |
| --- | --- |
| Cannabis powder | 2 |
| Gelucire ® 39/01 | 13.5 |
| Sodium benzoate | 0.7 |
| Potassium sorbate | 0.6 |
| Ethylenediaminetetraacetic acid | 0.15 |
| Citric acid | 0.6 |
| Bi-distilled water | 48.42 |
| Medium chain triglyceride oil | 1.6 |
| Kolliphor ® P407 | 2.3 |
| Ascorbyl palmitate | 0.07 |
| Mixed tocopherols | 0.06 |
| Polvoxyethylene sorbitan monooleate 80 | 5.2 |
| Lipoid ® P45 | 6.8 |
| Glycerin | 18 |
| Total | 100 |

Example 3: Stable Formulation of a Mixture of Cannabidiol Rich and Tetrahydrocannabinol Rich *Cannabis sativa*

The main active agents of *Cannabis sativa* are cannabinoids selected from the group of CBD, THC or combinations thereof. These cannabinoids may therefore be used as reference material to compare the concentration of different nano lipid formulations containing *Cannabis sativa* plant material. CBD rich strains (e.g. A6FS10 flos, AI Fame, Switzerland) or THC rich strains (e.g. Bedrocan flos, Bedrocan, Netherlands), or any combination thereof, may be used for the preparation of the aforementioned nano lipid formulation.

As an example, a formulation containing a mixture of the CBD rich *Cannabis sativa* strain A6FS10 flos (AI Fame, Switzerland) and the THC rich *Cannabis sativa* strain Bedrocan flos (Bedrocan, Netherlands) at a ratio of 2:1 (w/w), meaning 1.33% (w/w) A6FS10 and 0.67% (w/w) Bedrocan at a total *Cannabis* concentration of 2% (w/w) was prepared. Hence, 2% (w/w) decarboxylated and sterilized pre-ground *Cannabis sativa* powder ($D_{90}$<320 μm, residual moisture <3%) containing the aforementioned mixture of strains was prepared. Apart from the different types of *Cannabis sativa* material, the disclosed nano lipid formulation was prepared analogously to Example 2, using the mixed *Cannabis* powder instead of the pure cannabidiol rich *Cannabis* powder.

Example 4: Stable Formulation of Tetrahydrocannabinol Rich *Cannabis sativa* (1% (w/w))

Pre-ground and steam sterilized flower plant material from a tetrahydrocannabinol rich *Cannabis sativa* strain Bedrocan flos (Bedrocan, Netherlands), $D_{90}$<320 μm, residual moisture <10% was used as *Cannabis* powder.

Apart from the different type of *Cannabis sativa* material, the formulation of Example 4 was prepared analogously to Example 1.

Example 5: Stable Formulation of *Cannabis sativa* (1% (w/w))

Pre-ground and steam sterilized flower plant material from THC rich *Cannabis sativa* strain Bedrocan flos (Bedrocan, Netherlands) ($D_{90}$<320 μm, residual moisture <10%) was used as *Cannabis* powder. The *Cannabis* powder was inserted into a pre-heated oven chamber at 135° C. When the *Cannabis* powder has reached a core temperature of 128° C., the powder was subsequently heated for further 45 minutes at 135° C., in order to achieve decarboxylation of the active ingredients. This step further reduces the residual moisture in the *Cannabis* powder.

The amount of all ingredients is given in % (w/w), based on the total amount (mass) of the final nano-suspension.

7.8% (w/w) Gelucire™ 39/01 was pre-heated in a tempered water bath at 60° C., for one hour.

Separately, 0.9% (w/w) sodium benzoate, 0.6% (w/w) potassium sorbate, 0.45% (w/w) ethylenediaminetetraacetic acid, 0.75% (w/w) citric acid, and 0.1% (w/w) xanthan gum (Xanthural 11 K, CP Kelko, USA) were dispersed and thoroughly mixed in 56.34% (w/w) bi-distilled water and also pre-heated at 60° C., for one hour.

6.5% (w/w) medium chain triglyceride oil, 0.1% (w/w) ascorbyl palmitate, 0.06% (w/w) mixed tocopherols (Vitapherole®), 5.1% (w/w) polyoxyethylene sorbitan monooleate 80 (Tween® 80), and 4.3% (w/w) sorbitan monooleate (Span® 80) were mixed in a separate container.

All above listed compounds (except *Cannabis* powder) were combined in a suitable vessel at a temperature of 70° C.

Subsequently, 1% (w/w) decarboxylated and sterilized pre-ground *Cannabis sativa* powder material as prepared above ($D_{90}$<320 μm, residual moisture <3%) was carefully added to the degassed mixture and dispersed under continuous stirring. When dispersing the *Cannabis* material in the solvent, the *Cannabis* material in the formulation had a concentration of 1% (w/w), based on the total mass of the formulation.

The dispersion was subsequently milled in a wet ball agitator mill (type X1, Buehler AG, Switzerland; 1500 rpm, 45° C.) using yttrium stabilized zirconia balls of size 0.4 to 0.5 mm. The milling was continued until a monomodal particle size distribution of below 0.4 μm ($D_{100}$) was achieved. Subsequently, 16% (w/w) glycerin was added and milling was continued until reaching the final particle size ($D_{90}$) of the formulation of below 0.2 μm (200 nm), as measured by the laser diffraction device Beckman-Coulter LS13320

TABLE 3

Ingredients and amounts used in the formulation of Example 5

| Ingredient | Amount [% (w/w)] |
|---|---|
| Cannabis powder | 1 |
| Gelucire ® 39/01 | 7.8 |
| Sodium benzoate | 0.9 |
| Potassium sorbate | 0.6 |
| Ethylenediaminetetraacetic acid | 0.45 |
| Citric acid | 0.75 |
| Xanthan gum | 0.1 |
| Bi-distilled water | 56.34 |
| Medium chain triglyceride oil | 6.5 |
| Ascorbyl palmitate | 0.1 |
| Mixed tocopherols | 0.06 |
| Polyoxyethylene sorbitan monooleate 80 | 5.1 |
| Span ® 80 | 4.3 |
| Glycerin | 16 |
| Total | 100.0 |

Example 6: Determination of Plasma Concentrations of Cannabinol in a Pharmacokinetic Study A clinical trial in three healthy, male volunteers was performed to determine the pharmacokinetic effects of the cannabidiol rich *Cannabis* formulation (Example 1). A single dose of the *Cannabis* formulation containing 1.3 mg CBD was administered by oromucosal administration. Blood samples were taken immediately before dosing, and following administration of the *Cannabis* formulation after 10, 20, 30, 45, 60, and 90 minutes, as well as after 2, 3, 4, 5, 6, 7, 8, and 24 hours. Plasma concentration of CBD in the blood samples was determined by LC-MS/MS.

Figure 1:
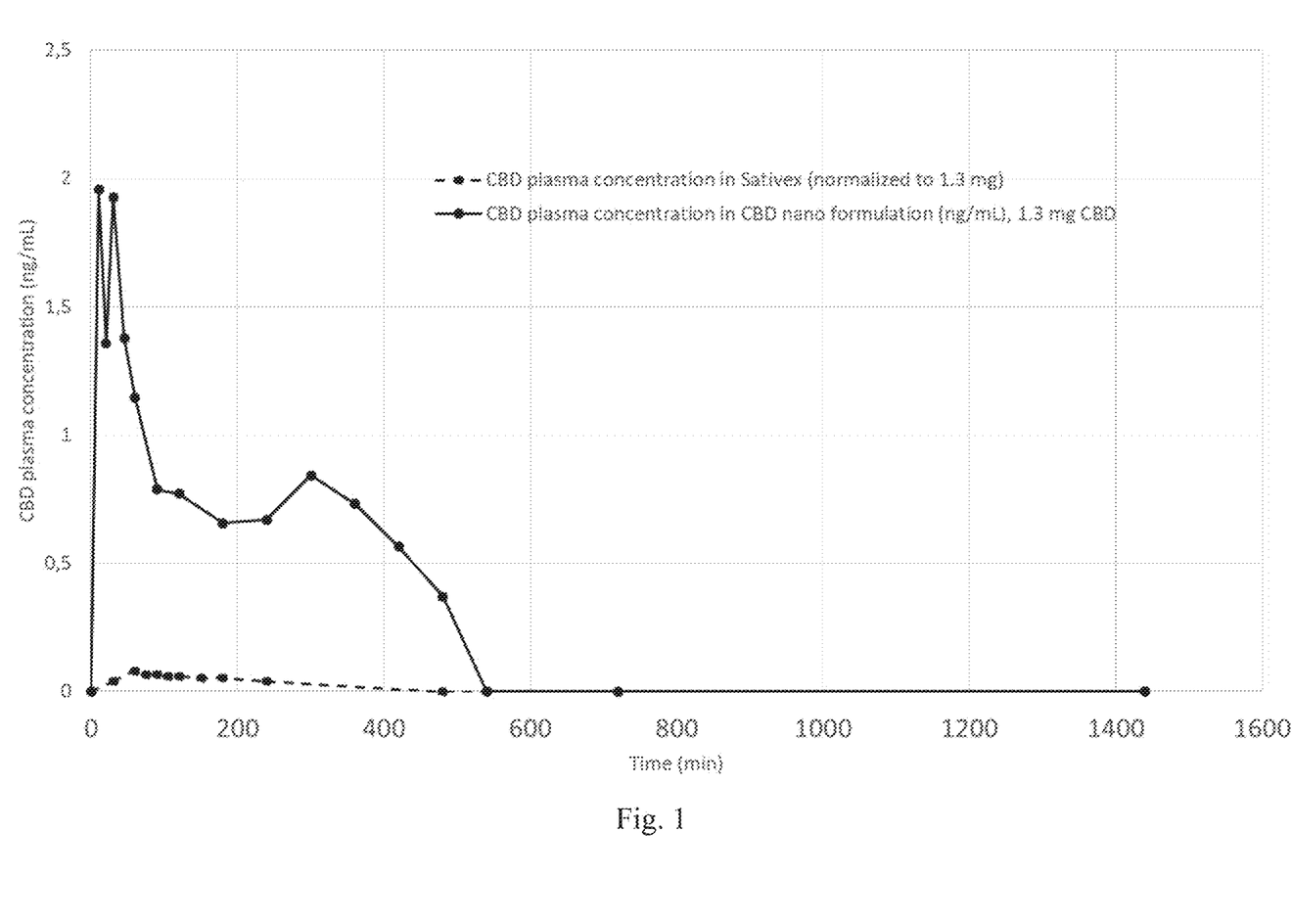
FIG. 1: Comparison of CBD plasma concentration after single dose administration of formulation of Example 1 with Sativex®.

Following administration of the *Cannabis* formulation, CBD is absorbed rapidly and is present in the plasma within 10 minutes after single dose oromucosal administration. A mean maximal concentration ($C_{max}$) of 1.96 ng/ml and an area under curve 0-24 hours (AUC 0-24 h) of 9.31 ng/ml*h was reached. $C_{max}$ and AUC levels of the formulation were compared to Sativex® Oromucosal Spray (GW Pharma Ltd) and listed in Table 4 (Stott et al., Eur J Clin Pharmacol 69 (2013), pages 1135-1147). The pharmacokinetic profile of the *Cannabis* formulation compared to the normalized single dose of Sativex® can be seen in FIG. 1. Compared to Sativex®, the CBD rich formulation of Example 1 shows increased AUC levels (factor 22.71) and increased $C_{max}$ concentrations (factor 19.60).

TABLE 4

Comparison of plasma concentrations and area under curve (AUC) values of CBD in CBD rich cannabis formulation with Sativex ® (normalized dose).

| Analyte CBD | CBD form. Ex. 1 (dose: 1.3 mg) | Sativex ® (dose: 5 mg) | Sativex ® normalized (dose: 1.3 mg) | Factor (CBD form. Ex. 1/Sativex ® norm.) |
|---|---|---|---|---|
| AUC [ng/ml * b] | 9.31 | 1.54 | 0.41 | 22.71 |
| $C_{max}$ [ng/ml] | 1.96 | 0.39 | 0.10 | 19.60 |

Example 7: Determination of Plasma Concentrations of Tetrahydrocannabinol and Main metabolites in a pharmacokinetic study A clinical trial in three healthy, male volunteers was performed to determine the pharmacokinetic effects of the tetrahydrocannabinol rich *Cannabis* formulation (Example 4). A single dose oromucosal administration of the *Cannabis* formulation containing 3.0 mg tetrahydrocannabinol was administered. Blood samples were taken immediately before dosing, and following administration of the *Cannabis* formulation after 2, 5, 10, 15, 20, 30, 45, 60, and 90 minutes, as well as after 2, 3, 4, 5, 6, 7, and 24 hours. Plasma concentration of THC in the blood samples was determined by LC-MS/MS.

Following administration of *Cannabis* nano-formulation, THC is absorbed and appears rapidly in the plasma within 15 minutes after single oromucosal administration. A mean maximal concentration ($C_{max}$) of 0.57 ng/ml and an area under curve 0-24 hours (AUC 0-24 h) of 6.94 ng/ml*h was reached. Mean concentrations and AUC levels of the THC plasma concentration were compared to a normalized dose of Sativex® oromucosal spray (GW Pharma Ltd) and listed in Table 5 (Stott et al., Eur J Clin Pharmacol 69 (2013), pages 1135-1147). The pharmacokinetic profile of the THC rich *Cannabis* formulation of Example 4 compared to the normalized single dose of Sativex® can be seen in FIG. 2.

Figure 2:
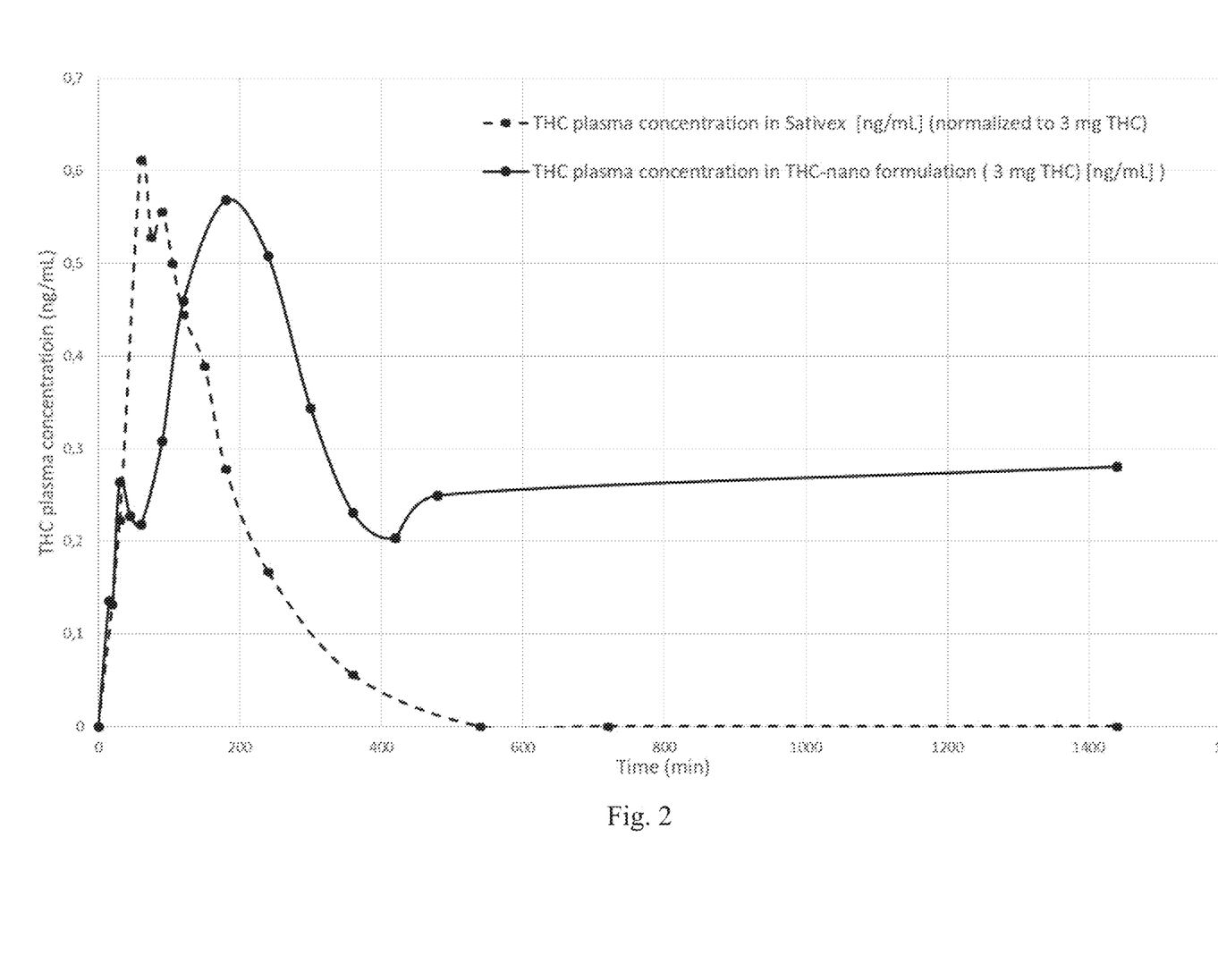
FIG. 2: Comparison of THC plasma concentration after single dose administration of formulation of Example 2 with Sativex®.

Compared to the oromucosal spray Sativex®, the THC rich formulation of Example 4 shows an increased AUC level (Factor 3.62). THC is highly lipophilic and is absorbed and distributed rapidly into body fat. The resultant concentrations and maximal concentrations in the blood following oromucosal administration of the formulation can vary depending on the composition of the formulation. However, the AUC values over 24 hours clearly demonstrate the enhanced bioavailability of the formulation of Example 4, compared to Sativex®.

TABLE 5

Comparison of pharmacokinetic results of THC in THC rich cannabis formulation of Example 4 with Sativex ® (normalized dose).

| Analyte THC | THC form. Ex. 4 (dose: 3 mg) | Sativex ® (dose: 5.4 mg) | Sativex ® normalized (dose: 3 mg) | Factor (THC formulation Ex. 4/Sativex ® norm.) |
|---|---|---|---|---|
| AUC [ng/ml * h] | 6.94 | 3.45 | 1.92 | 3.62 |
| Cmax [ng/ml] | 0.57 | 1.48 | 0.82 | 0.69 |

Example 8: Case Study with a Male Patient Suffering from Chronic Pain Due to Fibrosis Dysplasia, Treated with the Formulation of Example 4

A 54-year-old male patient suffering from chronic pain for 40 years due to fibrosis dysplasia and multiple operative bone correction underwent a pain therapy with the strong opioid fentanyl with a daily dosage of 36.000 μg i.v. The normal dosage for a chronic pain patient is 100 to 300 μg fentanyl as a patch which is changed every 3 days, resulting in about 100 μg fentanyl per day. The patient was highly addicted to opioid and sat in a wheel chair, due to the high fentanyl dosage. After the opioid withdrawal, he changed to a *Cannabis* oily extract with 800 mg THC dosage per day. Here he could reduce his pain level to 4 at a numerical rating scale (NRS) from 0) (meaning 0 pain) to 10 (maximum pain). The pain level of NRS=4 is referred to as baseline in the following. Without cannabinoid medication, he was at a pain level of 9. But the very high THC dosage of 800 mg daily caused severe psychotropic side effects. In Germany, the maximum allowable prescribed THC amount is 1000 mg per month.

The patient changed to the formulation of Example 4, which he took at a dosage of 28 mg THC per day from day 1 on, in exchange for his cannabinoid oily extract at a dosage of 800 mg THC. Within 14 days, the patient reduced the dosage of the formulation of Example 4 to 14.9 mg THC per day, and reduced the pain level from 4 to 1 (75% reduction from baseline), with a reduction of the THC dosage from 800 mg to 14.9 mg, meaning a THC dosage reduction by 98%. The patient was monitored over 12 months and he was at the end of the 12 months period still at a dosage of 14.9 mg THC of the formulation of Example 4 and at a pain level of 1.

Example 9: Case Study with a Male Patient Suffering from Spastic Due to Multiple Sclerosis Treated with the Formulation of Example 4

A 36-year-old male patient with a confirmed diagnosis of multiple sclerosis, anxiety disorder for more than 12 months, depression for more than 12 months, social phobia for more than 12 months, and multiple nerve damages for more than 12 months was treated under the following drug scheme: 2×300 mg/day pregabalin against neuropathic pain, venlafaxine 1×150 mg/day against anxiety disorder, dekristol 2000 IU (International Units) twice eper week against multiple sclerosis, copaxane 20 ml injection three times per week against multiple sclerosis. He had 5 to 9 spastic seizures per day, the severity of the spastic seizures was 4 on a NRS from 0 to 10 (10 maximum severity), and a pain level of his neuropathic pains at 3.

The patient took the formulation of Example 4 as co-medication to the above base medication, starting at a dosage of 12.1 mg THC, and reduced it to 7.5 mg THC/day within 5 weeks. Within 5 weeks, he could reduce the spastic seizures to 0 to 2 seizures per day (75% reduction from baseline), the severity of the spastic seizure to 2 (50% reduction from baseline), the pain level to 1 (67% reduction from baseline) at a 100% reduction of his base medication pregabalin from 2×300 mg/day to 0 mg/day.

Example 10: Case Study with a Female Patient Suffering from Fibromyalgia Treated with the Formulation of Example 4

A 51-year-old female patient with a confirmed diagnosis of fibromyalgia and a co-morbidity of anxiety disorder and depression taking doloxetin at 100 mg/day and 24.3 mg THC (Sativex®) per day. The patient was at a pain level of NRS=2. Without medication, she had a pain level of NRS=8. The patient wanted to change Sativex® due to ulceration in the oral mucosa. Ulceration of the oral mucosa is a well-known side effect of Sativex® due to its high alcohol content. She took the formulation of Example 4 in exchange to Sativex®. She started at a dosage of 2.8 mg THC with the formulation of Example 4 and kept this dosage within the therapy. She could reduce the pain level to NRS=1 (50% reduction from baseline) with a reduction of the THC dosage from 24.3 mg at Sativex® to 2.8 mg THC of the formulation of Example 4 (88% reduction).

Example 11: Case Study with a Female Patient Suffering from Primary Chronic Polyarthritis Treated with Formulation of Example 4

A 62-year-old female patient with a confirmed diagnosis of primary chronic polyarthritis since 42 years and a co-morbidity of anxiety disorder and depression with the following baseline medication: Celecoxib 200 mg twice daily (against pain), Tramadol 100 mg (against pain), Amitriptylineg/ml 5 drops (against anxiety disorder and depression). Aerius 5 mg once daily (against chronic urtikaria). She had the following co-morbidities; enteroparesis for more than 12 months, ectomy of the left breast after breast cancer, chronic bronchitis for more than 12 months, depression for more than 12 months, severe arthritis in both knee joints for more than 12 months. The patient was at a pain level of NRS=7 (baseline). Without medication she had a pain level of NRS=10.

She took the formulation of Example 4 as co-medication to the above base medication. She took 3.1 mg THC/day within a titration phase of 2 weeks. Within 2 weeks, she could reduce the pain level from NRS=7 to NRS=4 (43% reduction from baseline at a 50% reduction of the base medication celecoxib from 400 mg/day to 200 mg/day, and 100% reduction of tramadol from 37.5 mg/day to 0 mg/day.

Example 12: Reduction of 11-OH THC Level with Formulation of Example 4

Hydroxylation of THC at C(9) by CYP450 in the liver leads to the production of the pharmacological active metabolite 11-OH-THC. Originally, 11-OH-THC was known to be the major psychoactive substance (Huestis et al., 2007), although reliable data on the psychoactive effects in human is scarce. In some pharmacological animal experiments, 11-OH-THC was found to induce three to seven times more psychotropic side effects than THC (Grotenhermen et al., 2003, Lemberger et al., 1973). Additionally, penetration of 11 OH-THC into the brain appeared faster and at higher amounts, compared to THC (Perez-Reyes et al., 1976, Grotenhermen et al., 2003). Psychologic and physiologic effects of intravenously administered THC and 11-OH-THC in casual marihuana smokers were examined. Studies showed that tachycardia and psychological "high" occurred within 3-5 minutes after i.v, single dose administration of 11-OH-THC (dose: 1 mg).

The proportion of THC and 11-OH-THC as well as the onset of peak concentrations may have a dramatic influence on the effect and side effect profile of medical *Cannabis*. After smoking, peak 11-OH-THC concentrations occurred at approximately 13 minutes after application (Huestis et al., 1992). Following inhalational administration (e.g, smoking, vaporization), considerable low amounts of the active metabolite 11-OH-THC (23%) compared to 77% THC were reported, since the hepatic first-pass effect is avoided (Meyer et al. 2018, Spindle et al. 2016, Eisenberg et al., 2014).

For oral administration (dronabinol capsules and solution), a 3-fold higher formation of 11-OH-THC compared to THC can be found (Parikh et al., 2016). This can be attributed to the extensive hepatic first-pass metabolism following oral administration. Hunt et al, reported very high average plasma clearance rates of approximately 36 L/h for naïve THC users and 60 L/h for regular users, which are similar to the volume of hepatic blood flow. This indicates, that the limiting step of the metabolic rate is controlled by the hepatic blood flow. High clearance rates explain the high degree of first-pass metabolism and the considerable higher concentration of 11-OH-THC after oral administration compared to inhalation (Hunt et al. 1980, Grotenhermen et al., 2003). After administration of Sativex®, similar to oral delivery, a 3-fold higher formation of 11-OH-THC compared to THC can be found.

A clinical trial in three healthy, male volunteers was performed to determine the pharmacokinetic effects of the tetrahydrocannabinol rich *Cannabis* formulation (Example 4). A single dose oromucosal administration of the *Cannabis* formulation containing 3.0 mg tetrahydrocannabinol was administered. Blood samples were taken immediately before dosing, and following administration of the *Cannabis* formulation after 2, 5, 10, 15, 20, 30, 45, 60, and 90 minutes, as well as after 2, 3, 4, 5, 6, 7, and 24 hours. Plasma concentration of THC in the blood samples was determined by LC-MS/MS.

Following administration of *Cannabis* nano-formulation of Example 4, the 11-OH-THC level was significantly lower compared to Sativex® or dronabinol formulations. Mean concentrations and AUC levels of the THC plasma concentration were compared to a normalized dose of Sativex® oromucosal spray (GW Pharma Ltd.) (Stott et al., Eur J Clin Pharmacol 69 (2013), pages 1135-1147) and dronabinol (Parikh N, Kramer W G, Khurana V, *Cognata* Smith C, Vetticaden S (2016) Bioavailability study of dronabinol oral solution versus dronabinol capsules in healthy volunteers. Clin Pharmacol 8:155-162) and listed in Table 6.

Compared to the oromucosal spray Sativex® and dronabinol, the THC rich formulation of Example 4 shows a significantly lower 11-OH-THC AUC level (Factor 2.48 and 3.37, respectively). The significantly lower 11-OH-THC AUC values over 24 hours clearly demonstrate that the formulation of Example 4 is absorbed via the oral mucosa and avoids the first pass effect compared to Sativex® and dronabinol.

TABLE 6

Comparison of pharmacokinetic results of 11-OH-THC in THC rich cannabis formulation of Example 4 with Sativex ® and dronabinol (normalized dose).

| Product | AUC [ng/ml * h] of analyte 11-OH-THC |
|---|---|
| THC formulation of example 4 (dose: 3 mg) | 2.37 |
| Sativex ® (dose: 5.4 mg) | 10.58 |
| Sativex ® normalized (dose: 3 mg) | 5.88 |
| Factor (THC formulation Ex. 4/Sativex ® norm.) | 2.48 |
| dronabinol as capsule (dose: 5.0 mg) | 13.3 |
| dronabinol as capsule normalized (dose: 3 mg) | 7.98 |
| Factor (THC formulation Ex. 4/dronabinol capsule norm.) | 3.37 |

Embodiments

The present disclosure also relates to the following numbered embodiments.

1. A formulation comprising at least one natural *Cannabis* material, at least one solvent, and at least one stabilizer, wherein the formulation is a liquid suspension having a particle size ($D_{90}$) of below 500 nm.
2. The formulation of embodiment 1, wherein the at least one natural *Cannabis* material is a material of the family of Cannabaceae, preferably wherein the natural *Cannabis* material is a material of a genera selected from the group consisting of Aphananthe, *Cannabis, Celtis, Chaetachme, Gironniera, Humulus, Lozanella, Parasponia, Pteroceltis,* and *Trema*, and preferably wherein the natural *Cannabis* material is a material of genera *Cannabis*.
3. The formulation according to embodiment 2, wherein the at least one natural *Cannabis* material is a material of the genera *Cannabis*, and wherein the *Cannabis* is a species selected from the group consisting of *Cannabis sativa, Cannabis indica*, and *Cannabis ruderalis*, preferably wherein the at least one natural *Cannabis* material is a material of the species *Cannabis sativa*.
4. The formulation according to any one of the preceding embodiments, wherein the at least one natural *Cannabis* material is a mixture of at least two natural *Cannabis* materials, preferably two or three natural *Cannabis* materials, preferably a mixture of *Cannabis sativa* and *Cannabis* indica or *Cannabis ruderalis*.
5. The formulation according to any one of the preceding embodiments, wherein at the least one natural *Cannabis* material is a part or the whole of said natural *Cannabis* material, preferably wherein the part of said natural *Cannabis* material is selected from the group consisting of leave, stem, seed, flower, root, and mixtures thereof, and preferably wherein the natural *Cannabis* material comprises or is a flower of said natural *Cannabis* material.
6. The formulation according to any one of the preceding embodiments, wherein the at least one natural *Cannabis* material is present in an amount of from 0.1 to 20% (w/w), based on the total mass of the formulation, preferably from 0.1 to 10% (w/w), preferably from 0.2 to 5% (w/w), preferably from 0.3 to 4% (w/w), preferably from 0.5 to 3% (w/w), further preferably from 0.5 to 1% (w/w), from 1 to 2% (w/w), or from 2 to 4% (w/w), based on the total mass of the formulation.
7. The formulation according to any one of the preceding embodiments, wherein the solvent is selected from the group consisting of water, ethanol, a lipid, an apolar organic solvent, and a mixture thereof, preferably wherein the solvent is a mixture of water and a lipid.
8. The formulation according to embodiment 7, wherein the lipid is selected from the group consisting of a solid lipid, liquid lipid, waxes, and a mixture thereof, preferably wherein the lipid is a mixture of a liquid lipid and a solid lipid.
9. The formulation according to any one of embodiments 7 or 8, wherein the lipid is a glyceride, preferably selected from the group consisting of monoglycerides, diglycerides, or triglycerides, preferably wherein the lipid is a triglyceride, and more preferably wherein the glyceride is a mixture of a medium-chain triglyceride and glycerol esters of saturated $C_{12}$-$C_{18}$ fatty acids (Gelucir® 39/01).
10. The formulation according to any one of the preceding embodiments, wherein the stabilizer is selected from the group consisting of phospholipids; polysorbates; polymers comprising homopolymers, block and graft copolymers (comprising hydroxypropyl cellulose (HPC), hydroxypropyl methylcellulose (HPMC), and polyvinylpyrrolidone (PVP)); nonionic tri-block copolymers comprising poloxamers; copolyvinylpyrrolidone; Labrasol®; gelatin; lecithin (phosphatides); gum acacia; xanthan gum; gum arabica; cholesterol; tragacanth; polyoxyethylene alkyl ethers, polyoxyethylene castor oil derivatives; polyoxyethylene sorbitan fatty acid esters; sorbitan fatty acid esters; polyethylene glycols; polyoxyethylene stearates; colloidal silicon dioxide; sodium dodecylsulfate; mono and diglycerides; magnesium aluminum silicate; triethanolamine; stearic acid; calcium stearate; glycerol monostearate; cetostearyl alcohol; cetomacrogol emulsifying wax: short and medium chain alcohols; Labrafil®; Purololeique; propane-1,2,3-triol (glycerin); polyvinyl alcohol; dioctyl sodium sulfosuccinate (DOSS); carmellose sodium; carrageen; carbomer; hypromellose; and a mixture thereof.

11. The formulation according to any one of the preceding embodiments, wherein the stabilizer is selected from the group consisting of phospholipids, surfactants, and polymers, preferably wherein the stabilizer is a polymer selected from the group consisting of polysorbates, polysaccharides, and poloxamers.

12. The formulation according to embodiments 10 or 11, wherein the formulation comprises a polysorbate as stabilizer in an amount of up to 10% (w/w), based on the total mass of the formulation, preferably in an amount of from 0.5 to 4.5% (w/w), in an amount of from 1 to 4.5% (w/w), or in an amount of from 1.5 to 4% (w/w), more preferably in an amount of from 2 to 3% (w/w), or in an amount of from 3 to 4% (w/w), and most preferably in an amount of from 2.5 to 4% (w/w), and/or wherein the formulation comprises a polysorbate as stabilizer selected as polysorbate 80 (Tween® 80) or polysorbate 20 (Tween® 20), preferably polysorbate 80 (Tween® 80).

13. The formulation according to embodiments 10 to 12, wherein the formulation comprises a surfactant as stabilizer in an amount of up to 10% (w/w), based on the total mass of the formulation, preferably in an amount of from 0.5 to 4.5% (w/w), in an amount of from 1 to 4.5% (w/w), or in an amount of from 1.5 to 4% (w/w), more preferably in an amount of from 2 to 3% (w/w), or in an amount of from 3 to 4% (w/w), and most preferably in an amount of from 2.5 to 4% (w/w), and/or wherein the formulation comprises a surfactant as stabilizer selected as sorbitan monooleate (Span® 80).

14. The formulation according to any one of embodiments 10 to 13, wherein the formulation comprises a poloxamer as stabilizer in an amount of up to 10% (w/w), based on the total mass of the formulation, preferably in an amount of from 0.2 to 1.5% (w/w), more preferably in an amount of from 0.5 to 1% (w/w), and/or wherein the formulation comprises a poloxamer as stabilizer selected as poloxamer 407 (Kolliphor& P407), or poloxamer 188.

15. The formulation according to any one of embodiments 10 to 14, wherein the formulation comprises a polysaccharide as stabilizer in an amount of up to 5% (w/w), based on the total mass of the formulation, preferably in an amount of from 0.02 to 0.5% (w/w), in an amount of from 0.04 to 0.1% (w/w), more preferably in an amount of from 0.05 to 0.08% (w/w), and/or wherein the formulation comprises a polysaccharide as stabilizer selected as xanthan gum.

16. The formulation according to any one of embodiments 10 to 15, wherein the formulation comprises a phospholipid as stabilizer in an amount of from 0.5 to 10% (w/w), based on the total mass of the formulation, preferably in an amount of from 1 to 4% (w/w), and/or wherein the phospholipid contains phosphatidylcholine of from 40 to 100 (w/w), based on the total mass of phospholipid, and/or wherein the formulation comprises a phospholipid as stabilizer selected as Lipoid® P45.

17. The formulation according to any one of the preceding embodiments, wherein the formulation further comprises an additive, preferably wherein the additive is selected from the group consisting of preservatives, antioxidants, and osmotic agents.

18. The formulation according to embodiment 17, wherein the additive is a preservative, and wherein the preservative is present in the formulation in an amount of from 0.1 to 1% (w/w), based on the total mass of the formulation, preferably in an amount of from 0.10 to 0.15% (w/w), and/or wherein the formulation comprises a preservative as additive selected as potassium sorbate and/or sodium benzoate.

19. The formulation according to embodiment 17 or 18, wherein the additive is an antioxidant, and wherein the antioxidant is present in the formulation in an amount of from 0.01 to 3% (w/w), based on the total mass of the formulation, preferably in an amount of from 0.001 to 0.1% (w/w), in an amount of from 0.005 to 0.1% (w/w), 0.001 to 0.1% (w/w), in an amount of from 0.1 to 1% (w/w), or in an amount of up to 0.02% (w/w), and/or wherein the formulation comprises an antioxidant as additive selected from the group consisting of EDTA, tocopherols, citric acid, and ascorbyl palmitate.

20. The formulation according to any one of the preceding embodiments for use in palliative care, and/or in the treatment or alleviation of a disease, preferably wherein the disease is selected from the group consisting of pain, in particular acute or chronic pain, somatic pain, visceral pain, neuropathic pain, cancer pain, chronic back pain, chronic central nervous pain; neurological disorders, neurodegenerative diseases, insomnia, psychiatric disorders, nausea, anorexia, vomiting and nausea caused by chemotherapy, diabetic polyneuropathy, fibromyalgia, Tourette-Syndrome, multiple sclerosis, spasm at multiple sclerosis, anxiety disorders, schizophrenia, social phobia, sleep disorder, skin related diseases like psoriasis and neurodermatitis, glaucoma, restless leg syndrome, epilepsy, Alzheimer disease, movement disease like Dystonias, Huntington's disease, Parkinson's disease, bipolar disorder, as well as other medical indications which are affected by the endocannabinoid system and which are affected by any other receptors affected by cannabinoids (e.g., GPR18, GPR119, GPR55).

The invention claimed is:

1. A formulation comprising at least one natural *Cannabis* material, at least one solvent, and at least one stabilizer,
    wherein the formulation is a liquid suspension having a particle size ($D_{90}$) of below 500 nm.

2. The formulation of claim 1, wherein the at least one natural *Cannabis* material is a material of the family of Cannabaceae.

3. The formulation according to claim 2, wherein the at least one natural *Cannabis* material is a material of the genera *Cannabis*, and
    wherein the *Cannabis* is a species selected from the group consisting of *Cannabis sativa, Cannabis indica*, and *Cannabis ruderalis*.

4. The formulation according to claim 1, wherein the at least one natural *Cannabis* material is a part or the whole of said natural *Cannabis* material.

5. The formulation according to claim 1, wherein the at least one natural *Cannabis* material is dispersed in the formulation in an amount of from 0.1 to 20% (w/w), based on the total mass of the formulation.

6. The formulation according to claim 1, wherein the solvent is selected from the group consisting of water, ethanol, a lipid, an apolar organic solvent, and a mixture thereof.

7. The formulation according to claim 6, wherein the lipid is selected from the group consisting of a solid lipid, liquid lipid, waxes, and a mixture thereof.

8. The formulation according to claim 6, wherein the lipid is a glyceride.

9. The formulation according to claim 1, wherein the stabilizer is selected from the group consisting of phospholipids; polysorbates; polymers, block and graft copolymers; nonionic tri-block copolymers; copolyvinylpyrrolidone; caprylocaproyl polyoxyl-8 glycerides; gelatin; lecithin; gum acacia; xanthan gum; gum arabica; cholesterol; tragacanth; polyoxyethylene alkyl ethers; polyoxyethylene castor oil derivatives; polyoxyethylene sorbitan fatty acid esters; sorbitan fatty acid esters; polyethylene glycols; polyoxyethylene stearates; colloidal silicon dioxide; sodium dodecylsulfate; mono and diglycerides; magnesium aluminum silicate; triethanolamine; stearic acid; calcium stearate; glycerol monostearate; cetostearyl alcohol; cetomacrogol emulsifying wax; short and medium chain alcohols; oleoyl polyoxyl-6 glycerides; propane-1,2,3-triol; polyvinyl alcohol; dioctyl sodium sulfosuccinate; carmellose sodium; carrageen; carbomer; hypromellose; and a mixture thereof.

10. The formulation according to claim 1, wherein the stabilizer is selected from the group consisting of phospholipids, surfactants, and polymers.

11. The formulation according to claim 9, wherein the formulation comprises a polysorbate as the stabilizer in an amount of up to 10% (w/w), based on the total mass of the formulation, and/or wherein the formulation comprises a polysorbate as the stabilizer, selected from the group consisting of polysorbate 80 and polysorbate 20.

12. The formulation according to claim 9, wherein the polymers are selected from the group consisting of homopolymers,
wherein the block and graft copolymers are selected from the group consisting of hydroxypropyl cellulose (HPC), hydroxypropyl methylcellulose (HPMC), and polyvinylpyrrolidone (PVP), and
wherein the nonionic tri-block copolymers are selected from the group consisting of poloxamers.

13. The formulation according to claim 9, wherein the formulation comprises a phospholipid as the stabilizer in an amount of from 0.5 to 10% (w/w), based on the total mass of the formulation, and/or wherein the phospholipid contains phosphatidylcholine of from 40 to 100% (w/w), based on the total mass of phospholipid, and/or wherein the formulation comprises a fat-free soybean lecithin comprising phosphatidylcholine as the stabilizer.

14. The formulation according to claim 1, wherein the formulation further comprises an additive.

15. A method of providing palliative care and/or of treating or alleviating a disease in a subject in need thereof, the method comprising:
administering the formulation according to claim 1 to the subject, in an amount effective for use in the palliative care, and/or in the treatment or alleviation of the disease.

16. The formulation according to claim 1, wherein the natural *Cannabis* material is not an extract.

17. The formulation according to claim 4, wherein the part of said *Cannabis* material is selected from the group consisting of leaf, stem, seed, flower, root, and mixtures thereof.

18. The formulation according to claim 12, wherein the formulation comprises a poloxamer as the stabilizer in an amount of up to 10% (w/w), based on the total mass of the formulation, and/or wherein the formulation comprises a poloxamer as the stabilizer selected from the group consisting of poloxamer 407 and poloxamer 188.

19. The method according to claim 15, wherein the disease is selected from the group consisting of pain, neurological disorders, neurodegenerative diseases, insomnia, psychiatric disorders, nausea, anorexia, vomiting and nausea caused by chemotherapy, diabetic polyneuropathy, fibromyalgia, Tourette-Syndrome, multiple sclerosis, spasm at multiple sclerosis, anxiety disorders, schizophrenia, social phobia, sleep disorder, skin related diseases, glaucoma, restless leg syndrome, epilepsy, Alzheimer's disease, movement disease, Huntington's disease, Parkinson's disease, and other medical indications which are affected by the endocannabinoid system and which are affected by any other receptors affected by cannabinoids.

20. The method according to claim 19, wherein the pain is selected from the group consisting of acute pain, chronic pain, somatic pain, visceral pain, neuropathic pain, cancer pain, chronic back pain, and chronic central nervous pain.

21. The formulation according to claim 1, wherein CBD is absorbed rapidly from the formulation and is present in plasma within 10 minutes after a single dose oromucosal administration.

22. The formulation according to claim 1, wherein THC is absorbed from the formulation and appears rapidly in plasma within 15 minutes after a single oromucosal administration.

* * * * *